United States Patent
Pool et al.

(10) Patent No.: US 9,179,938 B2
(45) Date of Patent: Nov. 10, 2015

(54) DISTRACTION DEVICES AND METHOD OF ASSEMBLING THE SAME

(71) Applicant: ELLIPSE TECHNOLOGIES, INC., Irvine, CA (US)

(72) Inventors: Scott Pool, Laguna Hills, CA (US); Arvin Chang, Yorba Linda, CA (US)

(73) Assignee: Ellipse Technologies, Inc., Aliso Viejo, CA (US)

( * ) Notice: Subject to any disclaimer, the term of this patent is extended or adjusted under 35 U.S.C. 154(b) by 183 days.

(21) Appl. No.: 13/791,430

(22) Filed: Mar. 8, 2013

(65) Prior Publication Data

US 2014/0250674 A1 Sep. 11, 2014

(51) Int. Cl.
*A61B 17/70* (2006.01)
*B23P 11/00* (2006.01)
*A61B 17/68* (2006.01)

(52) U.S. Cl.
CPC .............. *A61B 17/7016* (2013.01); *A61B 17/68* (2013.01); *A61B 17/702* (2013.01); *A61B 17/7008* (2013.01); *A61B 17/7068* (2013.01);
(Continued)

(58) Field of Classification Search
CPC .............. A61B 17/68; A61B 17/7016; A61B 17/7001; A61B 17/7002; A61B 17/7004; A61B 17/7005; A61B 17/7008; A61B 17/7019; A61B 17/7014; A61B 17/701; A61B 17/702; A61B 17/7068; A61B 17/7216; A61B 2017/681; A61B 2017/0256; Y10T 29/49963; Y10T 29/49947; Y10T 29/49966; Y10T 29/49881
USPC ...................... 29/525.11, 525.01, 525.13, 456
See application file for complete search history.

(56) References Cited

U.S. PATENT DOCUMENTS 2,702,031 A * 2/1955 Wenger ........................... 606/51
4,931,055 A * 6/1990 Bumpus et al. .................. 606/60
(Continued)

FOREIGN PATENT DOCUMENTS

| WO | WO 8707134 A1 * | 12/1987 | ........... A61B 17/60 |
| WO | WO 2006/103071 | 10/2006 | |
| WO | WO 2008003952 A1 | 1/2008 | |
| WO | WO 2010/050891 A1 | 5/2010 | |

OTHER PUBLICATIONS

Verkerke, G. J. et al., Design of a lengthening element for a modular femur endoprosthetic system, Proc Instn Mech Engrs, vol. 203, 6 pages (1989).

(Continued)

*Primary Examiner* — Essama Omgba
(74) *Attorney, Agent, or Firm* — Knobbe, Martens, Olson & Bear, LLP

(57) ABSTRACT

A method of assembling a system for manipulating the skeletal system includes obtaining a monolithic member having opposing ends, one end including a housing having an axially extending cavity. A distraction rod is obtained that has opposing ends, a first end having an inner threaded cavity. A rotatable, radially poled magnet is rotationally coupled to a lead screw having threads. The threads of the lead screw are engaged with the threaded cavity of the distraction rod. The magnet and at least a portion of the first end of the distraction rod are inserted into the axially extending cavity such that the distraction rod and the monolithic member are in coaxial relation to one another. The magnet is axially locked in relation to the monolithic member, wherein the axially locked magnet is capable of rotation. The distraction rod is rotationally locked in relation to the monolithic member.

20 Claims, 14 Drawing Sheets

(52) U.S. Cl.
CPC ...... *Y10T 29/49963* (2015.01); *Y10T 29/49966* (2015.01)

(56) References Cited

U.S. PATENT DOCUMENTS

| | | | |
|---|---|---|---|
| 5,575,790 A | 11/1996 | Chen et al. | |
| 5,704,939 A | 1/1998 | Justin | |
| 6,033,412 A | 3/2000 | Losken et al. | |
| 6,336,929 B1* | 1/2002 | Justin | 606/63 |
| 6,375,682 B1 | 4/2002 | Fleischmann et al. | |
| 6,416,516 B1 | 7/2002 | Stauch et al. | |
| 6,417,750 B1 | 7/2002 | Sohn | |
| 6,706,042 B2 | 3/2004 | Taylor | |
| 6,730,087 B1 | 5/2004 | Butsch | |
| 6,849,076 B2 | 2/2005 | Blunn et al. | |
| 7,063,706 B2 | 6/2006 | Wittenstein | |
| 7,105,029 B2* | 9/2006 | Doubler et al. | 623/22.42 |
| 7,135,022 B2 | 11/2006 | Kosashvili et al. | |
| 7,357,635 B2 | 4/2008 | Belfor et al. | |
| 7,458,981 B2 | 12/2008 | Fielding | |
| 7,481,841 B2 | 1/2009 | Hazerbrouck et al. | |
| 7,530,981 B2 | 5/2009 | Kutsenko | |
| 7,531,002 B2 | 5/2009 | Sutton et al. | |
| 7,559,951 B2 | 7/2009 | DiSilvestro et al. | |
| 7,601,156 B2 | 10/2009 | Robinson | |
| 7,611,526 B2 | 11/2009 | Carl et al. | |
| 7,666,184 B2 | 2/2010 | Stauch | |
| 7,708,737 B2 | 5/2010 | Kraft et al. | |
| 7,753,915 B1 | 7/2010 | Eksler et al. | |
| 7,763,053 B2 | 7/2010 | Gordon | |
| 7,776,091 B2 | 8/2010 | Mastrorio et al. | |
| 7,794,476 B2 | 9/2010 | Wisnewski | |
| 7,811,328 B2 | 10/2010 | Molz, IV et al. | |
| 7,862,502 B2 | 1/2011 | Pool et al. | |
| 7,887,566 B2 | 2/2011 | Hynes | |
| 7,955,357 B2* | 6/2011 | Kiester | 606/258 |
| 7,981,025 B2 | 7/2011 | Pool et al. | |
| 8,043,299 B2 | 10/2011 | Conway | |
| 8,057,472 B2 | 11/2011 | Walker et al. | |
| 8,105,363 B2 | 1/2012 | Fielding et al. | |
| 8,147,517 B2 | 4/2012 | Trieu et al. | |
| 8,147,549 B2 | 4/2012 | Metcalf et al. | |
| 8,177,789 B2 | 5/2012 | Magill et al. | |
| 8,197,490 B2 | 6/2012 | Pool et al. | |
| 8,211,179 B2 | 7/2012 | Molz, IV et al. | |
| 8,216,275 B2 | 7/2012 | Fielding et al. | |
| 8,221,420 B2 | 7/2012 | Keller | |
| 8,241,331 B2 | 8/2012 | Arnin | |
| 8,246,533 B2 | 8/2012 | Chang et al. | |
| 8,252,063 B2 | 8/2012 | Stauch | |
| 8,282,671 B2 | 10/2012 | Connor | |
| 8,298,240 B2 | 10/2012 | Giger et al. | |
| 8,343,192 B2* | 1/2013 | Kiester | 606/279 |
| 8,382,756 B2 | 2/2013 | Pool et al. | |
| 8,419,801 B2 | 4/2013 | DiSilvestro et al. | |
| 8,439,915 B2 | 5/2013 | Harrison et al. | |
| 8,449,543 B2* | 5/2013 | Pool et al. | 606/63 |
| 8,469,908 B2 | 6/2013 | Asfora | |
| 8,486,110 B2 | 7/2013 | Fielding et al. | |
| 8,529,606 B2 | 9/2013 | Alamin et al. | |
| 8,562,653 B2 | 10/2013 | Alamin et al. | |
| 8,568,457 B2 | 10/2013 | Hunziker | |
| 8,632,544 B2 | 1/2014 | Haaja et al. | |
| 8,632,548 B2* | 1/2014 | Soubeiran | 606/90 |
| 8,641,723 B2 | 2/2014 | Connor | |
| 8,657,856 B2* | 2/2014 | Gephart et al. | 606/254 |
| 8,663,285 B2 | 3/2014 | Dall et al. | |
| 8,715,282 B2* | 5/2014 | Pool | 606/62 |
| 8,734,488 B2* | 5/2014 | Pool et al. | 606/258 |
| 8,777,947 B2 | 7/2014 | Zahrly et al. | |
| 8,790,409 B2 | 7/2014 | Van den Heuvel et al. | |
| 8,852,187 B2* | 10/2014 | Pool et al. | 606/63 |
| 8,852,236 B2* | 10/2014 | Kiester | 606/258 |
| 8,870,959 B2 | 10/2014 | Arnin | |
| 8,894,663 B2 | 11/2014 | Giger et al. | |
| 8,961,567 B2 | 2/2015 | Hunziker | |
| 8,968,406 B2 | 3/2015 | Arnin | |
| 8,974,463 B2* | 3/2015 | Pool | A61B 17/7004 606/105 |
| 8,992,527 B2 | 3/2015 | Guichet | |
| 9,022,917 B2 | 5/2015 | Kasic et al. | |
| 2003/0149487 A1* | 8/2003 | Doubler et al. | 623/23.44 |
| 2004/0023623 A1 | 2/2004 | Stauch et al. | |
| 2005/0090823 A1 | 4/2005 | Bartim | |
| 2005/0159754 A1 | 7/2005 | Odrich | |
| 2005/0234448 A1 | 10/2005 | McCarthy | |
| 2005/0246034 A1 | 11/2005 | Soubeiran | |
| 2005/0261779 A1* | 11/2005 | Meyer | 623/23.47 |
| 2006/0004459 A1* | 1/2006 | Hazebrouck et al. | 623/18.12 |
| 2006/0009767 A1* | 1/2006 | Kiester | 606/61 |
| 2006/0047282 A1* | 3/2006 | Gordon | 606/61 |
| 2006/0204154 A1* | 9/2006 | Ward | 384/100 |
| 2006/0235424 A1 | 10/2006 | Vitale et al. | |
| 2006/0293683 A1 | 12/2006 | Stauch | |
| 2007/0010814 A1 | 1/2007 | Stauch | |
| 2007/0264605 A1 | 11/2007 | Belfor et al. | |
| 2007/0270803 A1 | 11/2007 | Giger et al. | |
| 2007/0276378 A1 | 11/2007 | Harrison et al. | |
| 2008/0161933 A1 | 7/2008 | Grotz et al. | |
| 2008/0167685 A1 | 7/2008 | Allard et al. | |
| 2008/0228186 A1 | 9/2008 | Gall et al. | |
| 2008/0255615 A1 | 10/2008 | Vittur et al. | |
| 2009/0076597 A1 | 3/2009 | Dahlgren et al. | |
| 2009/0093890 A1 | 4/2009 | Gelbart | |
| 2009/0171356 A1 | 7/2009 | Klett | |
| 2009/0192514 A1 | 7/2009 | Feinberg et al. | |
| 2009/0254088 A1 | 10/2009 | Soubeiran | |
| 2009/0275984 A1 | 11/2009 | Kim et al. | |
| 2010/0004654 A1* | 1/2010 | Schmitz et al. | 606/90 |
| 2010/0049204 A1 | 2/2010 | Soubeiran | |
| 2010/0100185 A1 | 4/2010 | Trieu et al. | |
| 2010/0217271 A1* | 8/2010 | Pool et al. | 606/90 |
| 2010/0249847 A1 | 9/2010 | Jung et al. | |
| 2011/0054535 A1* | 3/2011 | Gephart et al. | 606/259 |
| 2011/0137347 A1 | 6/2011 | Hunziker | |
| 2011/0230883 A1 | 9/2011 | Zahrly et al. | |
| 2011/0238126 A1 | 9/2011 | Soubeiran | |
| 2011/0257655 A1 | 10/2011 | Copf et al. | |
| 2012/0004494 A1 | 1/2012 | Payne et al. | |
| 2012/0053633 A1 | 3/2012 | Stauch | |
| 2012/0088953 A1 | 4/2012 | King | |
| 2012/0109207 A1 | 5/2012 | Trieu | |
| 2012/0130428 A1 | 5/2012 | Hunziker | |
| 2012/0197262 A1 | 8/2012 | Heilman | |
| 2012/0203282 A1 | 8/2012 | Sachs et al. | |
| 2012/0232834 A1 | 9/2012 | Roche et al. | |
| 2012/0283781 A1 | 11/2012 | Arnin | |
| 2013/0072932 A1 | 3/2013 | Stauch et al. | |
| 2013/0096615 A1* | 4/2013 | Kiester | 606/258 |
| 2013/0138017 A1 | 5/2013 | Jundt et al. | |
| 2013/0150709 A1 | 6/2013 | Baumgartner | |
| 2013/0150863 A1 | 6/2013 | Baumgartner | |
| 2013/0150889 A1 | 6/2013 | Fening et al. | |
| 2013/0253344 A1 | 9/2013 | Griswold et al. | |
| 2013/0296940 A1 | 11/2013 | Northcutt et al. | |
| 2014/0005788 A1 | 1/2014 | Haaja et al. | |
| 2014/0025172 A1 | 1/2014 | Lucas et al. | |
| 2014/0128920 A1 | 5/2014 | Kantelhardt | |
| 2014/0142631 A1 | 5/2014 | Hunziker | |
| 2014/0250706 A1* | 9/2014 | Pool et al. | 29/525.11 |
| 2014/0257412 A1* | 9/2014 | Patty et al. | 606/308 |
| 2014/0296918 A1 | 10/2014 | Fening et al. | |
| 2014/0324047 A1 | 10/2014 | Zahrly et al. | |
| 2014/0371796 A1* | 12/2014 | Kiester | 606/258 |
| 2015/0105824 A1 | 4/2015 | Moskowitz et al. | |

OTHER PUBLICATIONS

Verkerke, G. J. et al., Development and test of an extendable endoprothesis for bone reconstruction in the leg, The International Journal of Artificial Organs, vol. 17, No. 3, 1994, pp. 155-162.

(56) References Cited

OTHER PUBLICATIONS

Stokes O., O'Donovan E., Samartzis D., Cora B., Luk K., Cheung K., "Reducing Radiation Exposure in Early-Onset Scoliosis Patients: Novel use of Ultrasonography to Measure Lengthening in Magnetically-Controlled Growing Rods. Prospective Validation Study and Assessment of Clinical Algorithm", 20th International Meeting on Advanced Spine Techniques, Jul. 11, 2013. Vancouver, Canada. Scoliosis Research Society.

Baumgart, R., Betz, A., Schweiberer, L, "A Fully Implantable Motorized Intramedullary Nail for Limb Lengthening and Bone Transport", Clinical Orthopaedics and Related Research, 1997, No. 343, pp. 135-143.

Cole, J., Justin, D., Kasparis, T., De Vlught, D., Knobloch, C., "The Intramedullary Skeletal Kinetic Distractor (ISKD): First Clinical Results of a New Intramedullary Nail for Lengthening of the Femur and Tibia", Injury, 2001, vol. 32, pp. S-D-129-S-D-139.

Guichet, J., Deromedis, B., Donnan, L, Peretti, G., Lascombes, P., Bado, F., "Gradual Femoral Lengthening with the Albizzia Intramedullary Nail", The Journal of Bone & Joint Surgery, 2003, vol. 85A, pp. 838-848.

Thonse, R., Herzenberg, J., Standard, S., Paley, D., "Limb Lengthening with a Fully Implantable, Telescopic, Intramedullary Nail", Operative Techniques in Orthopaedics, 2005, vol. 15, pp. 355-362.

Baumgart, R., Hinterwimmer, S., Krammer, M., Muensterer, O., Muschler, W., "The Bioexpandable Prosthesis: A New Perspective after Resection of Malignant Bone Tumors in Children", Journal of Pediatric Hemotology/Oncology, 2005, vol. 27, No. 8, pp. 452-455.

Baumgart, R., Thaller, P., Hinterwimmer, S., Krammer, M., Hierl, T., Mutschler, W., "A Fully Implantable, Programmable Distraciton Nail (Fitbone)—New Perspectives for Corrective and Reconstructive Limb Surgery", in Practice of Intramedullary Locked Nails, 2006, pp. 189-198.

Hofmeister, M., Hierholzer, C., Bühren, V., "Callus Distraction with the Albizzia Nail", in Practice of Intramedullary Locked Nails, 2006, pp. 211-215.

Krieg, A., Speth, B., Foster, B., "Leg Lengthening with a Motorized Nail in Adolescents", Clinical Orthopaedics and Related Research, 2008, No. 466, pp. 189-197.

Simpson, A., Shalaby, H., Keenan, G., "Femoral Lengthening with the Intramedullary Skeletal Kinetic Distractor", The Journal of Bone & Joint Surgery, 2009, vol. 91B, pp. 955-961.

Kenawey, M., Krettek, C., Liodakis, E., Wiebking, U., Hankemeier, S., "Leg Lengthening Using Intramedullary Skeletal Kinetic Distractor: Results of 57 Consecutive Applications", Injury, 2011, vol. 42, pp. 150-155.

Burghardt, R., Herzenberg, J., Specht, S., Paley, D., "Mechanical Failure of the Intramedullary Skeletal Kinetic Distractor in Limb Lengthening", The Journal of Bone 7 Joint Surgery, 2011, vol. 93B, pp. 639-643.

Thaller, P., Fürmetz, J., Wolf, F., Eilers, T., Mutschler, W., "Limb lengthening with fully implantable magnetically actuated mechanical nails (PHENIX1)—Preliminary results", Injury, 2014, vol. 45, Suppl. 1, pp. S60-S65, E-published Oct. 28, 2013.

\* cited by examiner

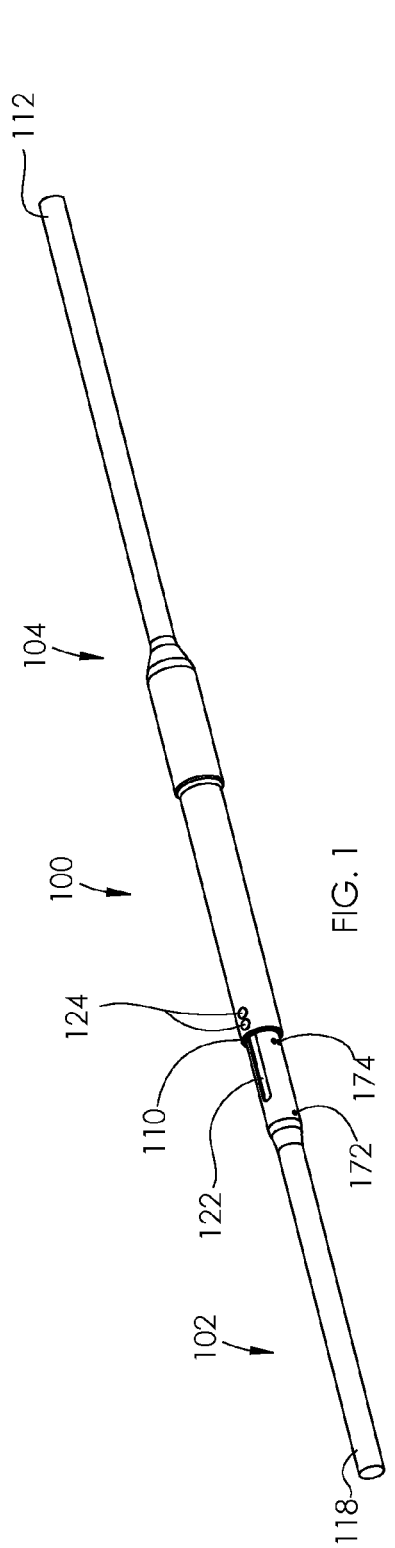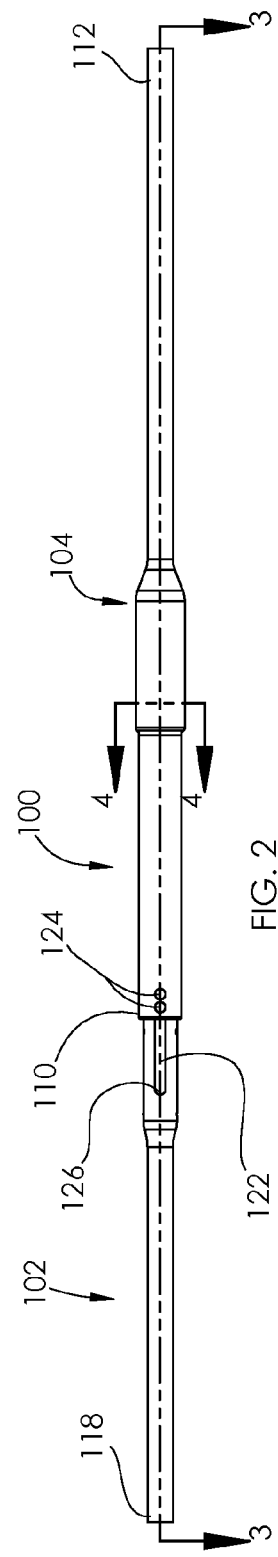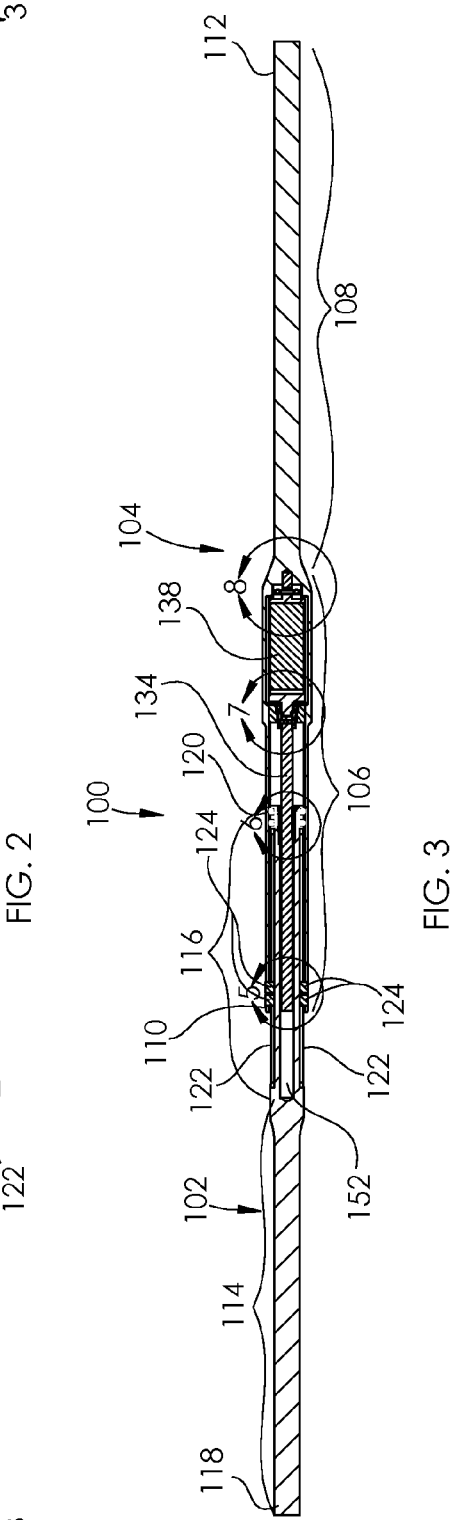

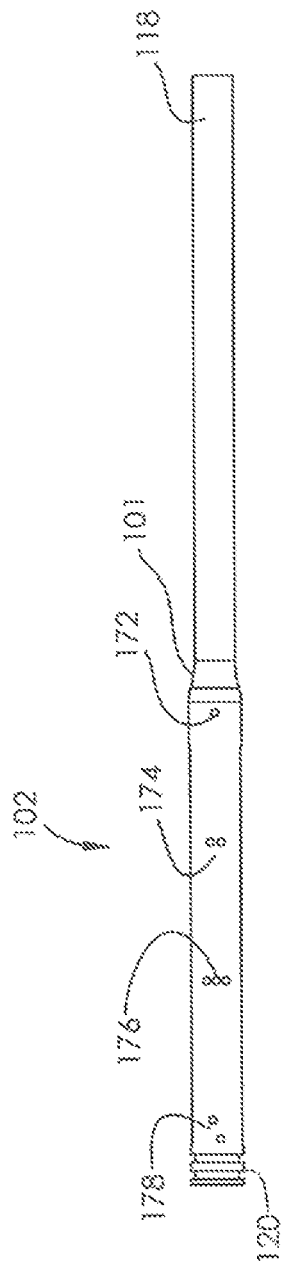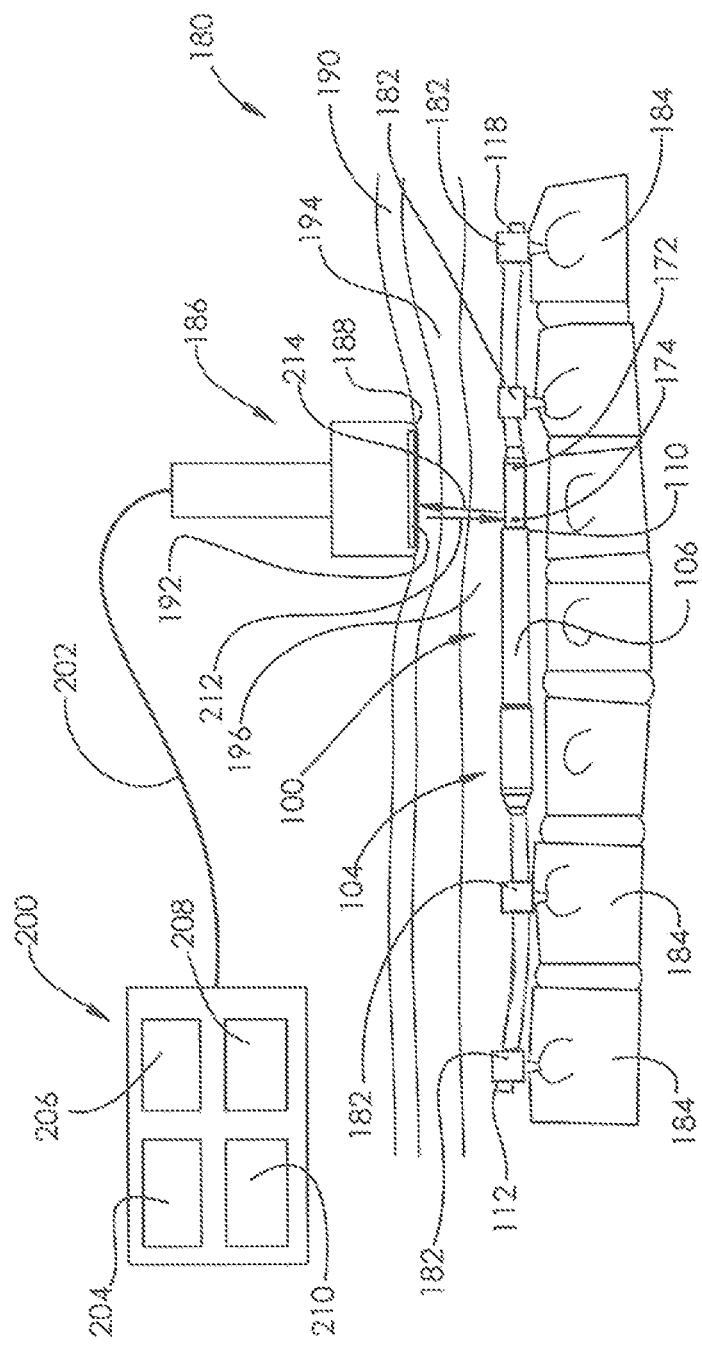

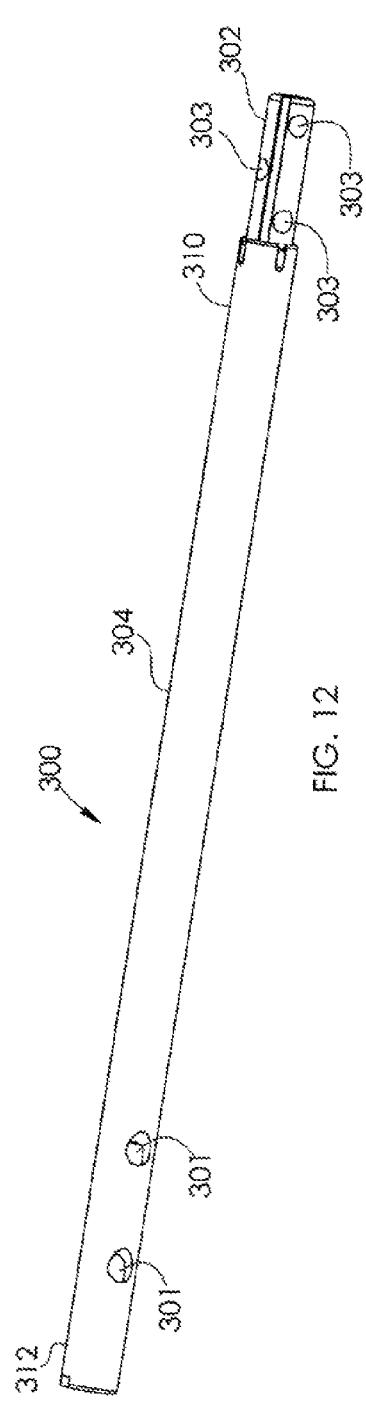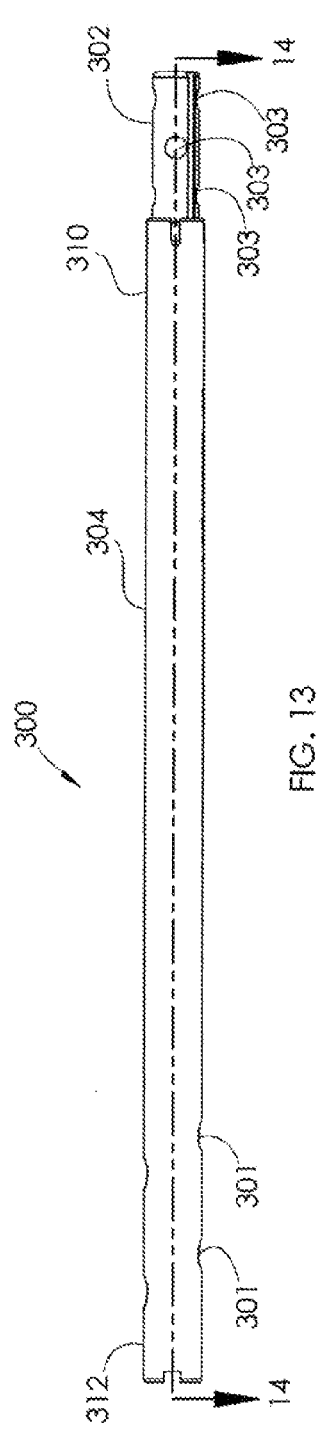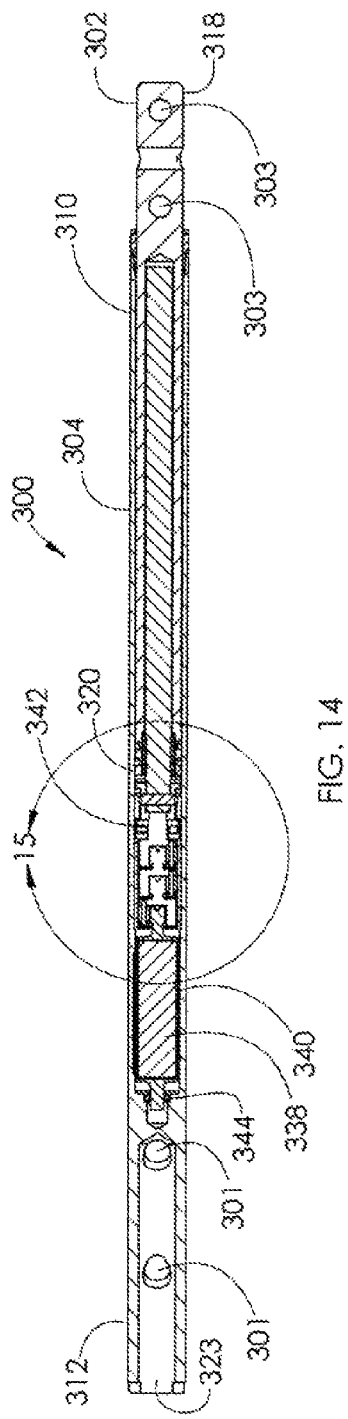

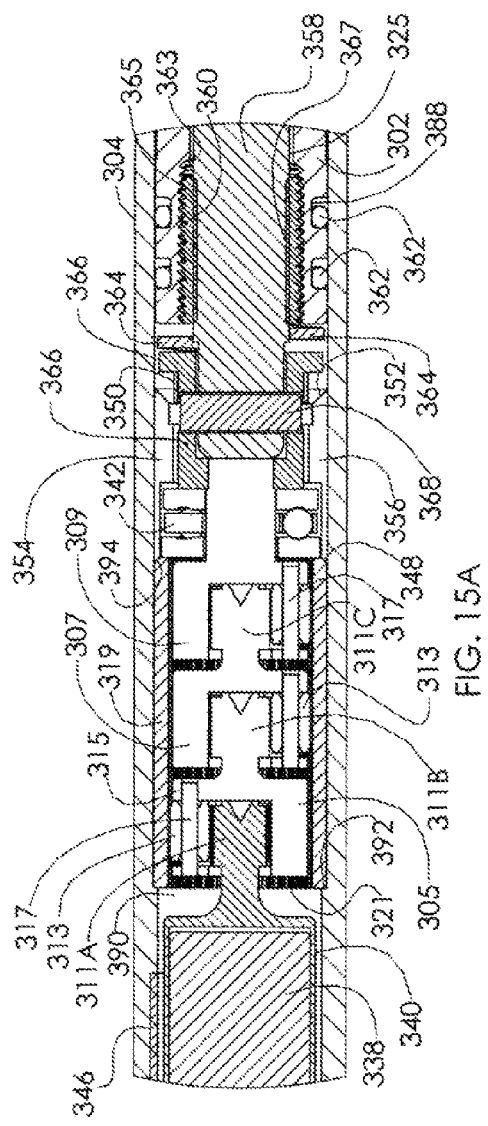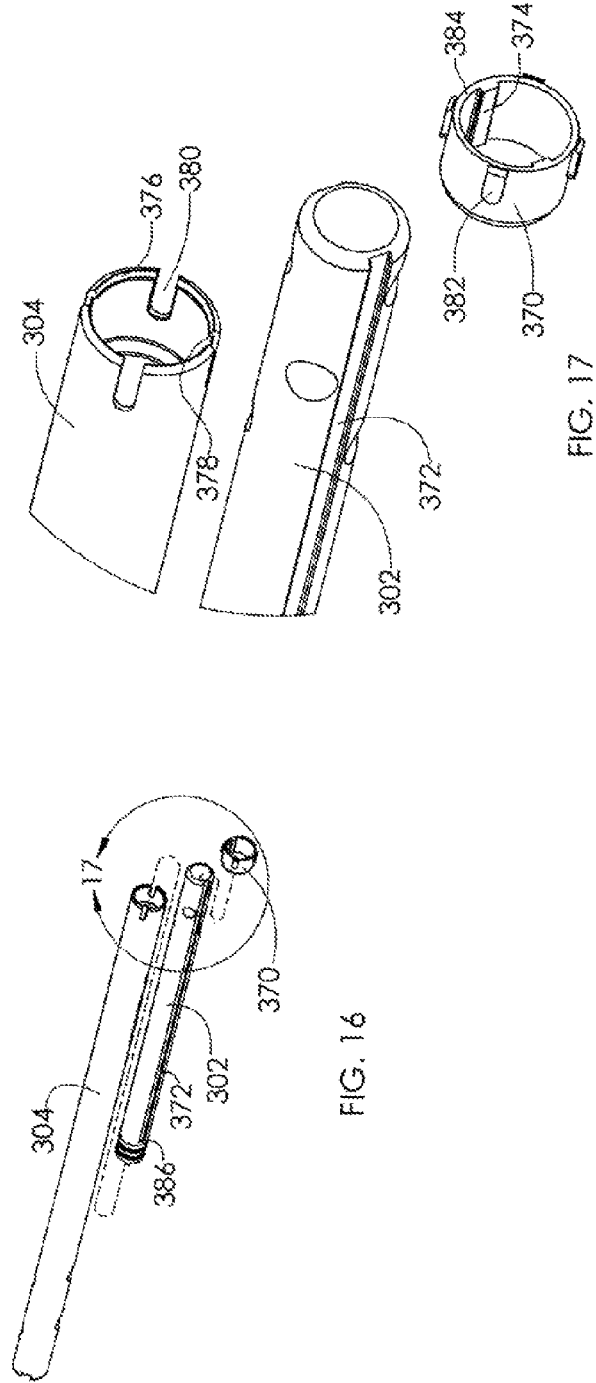

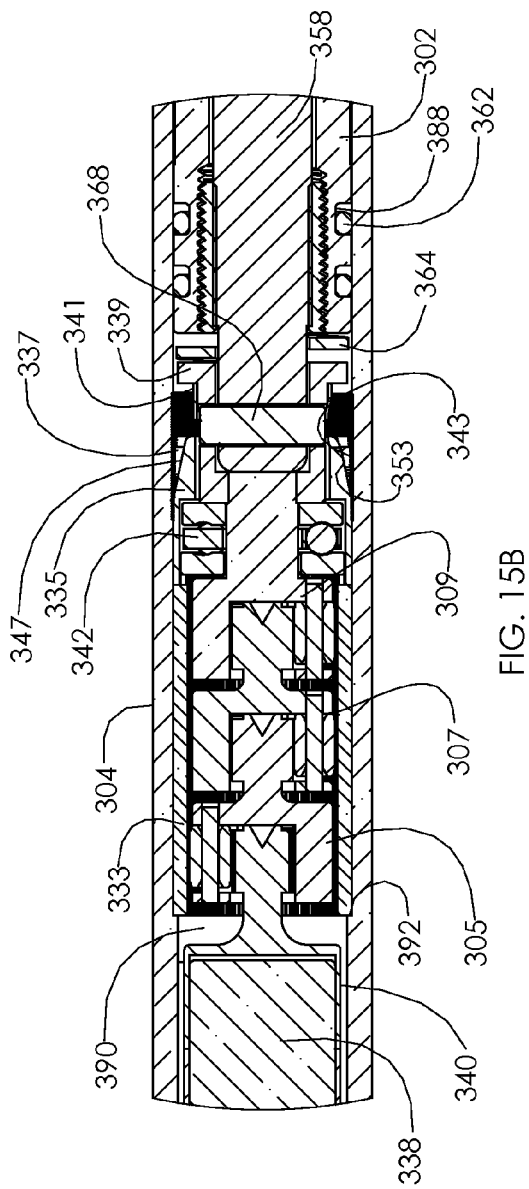
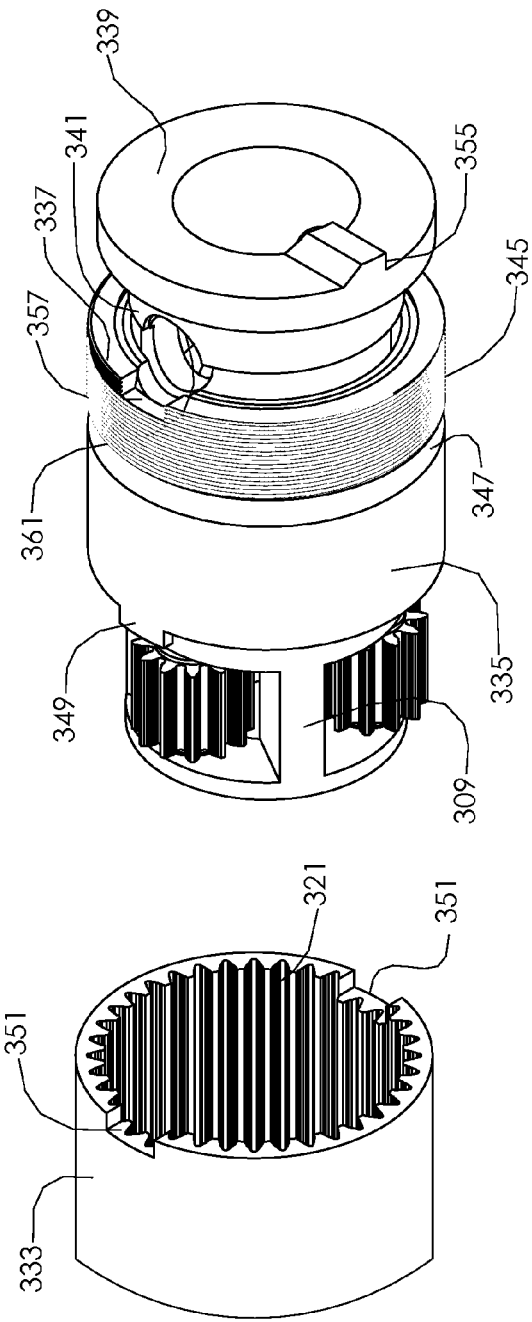

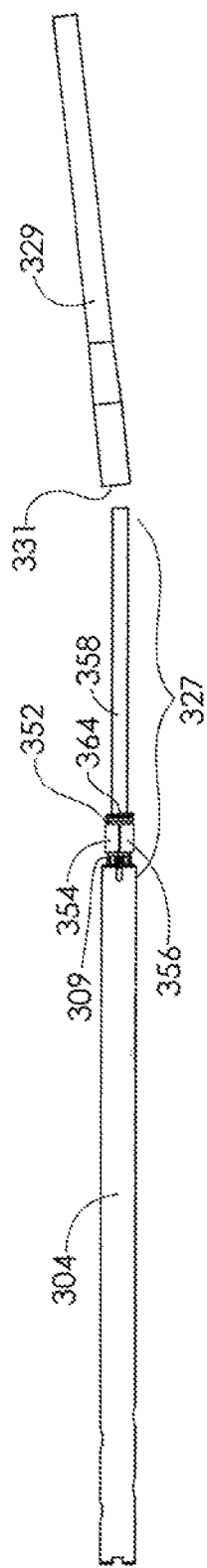
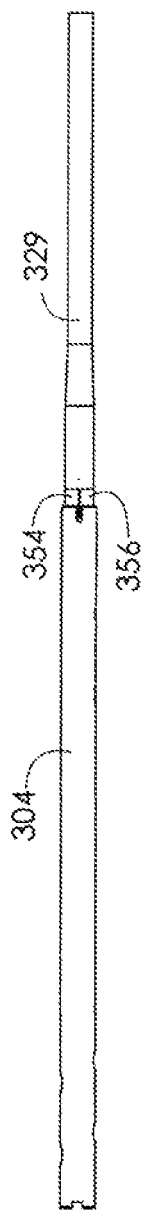

DISTRACTION DEVICES AND METHOD OF ASSEMBLING THE SAME

FIELD OF THE INVENTION

The field of the invention generally relates to medical devices for treating disorders of the skeletal system.

BACKGROUND

Distraction osteogenesis is a technique which has been used to grow new bone in patients with a variety of defects. For example, limb lengthening is a technique in which the length of a bone (for example a femur or tibia) may be increased. By creating a corticotomy, or osteotomy, in the bone, which is a cut through the bone, the two resulting sections of bone may be moved apart at a particular rate, such as one (1.0) mm per day, allowing new bone to regenerate between the two sections as they move apart. This technique of limb lengthening is used in cases where one limb is longer than the other, such as in a patient whose prior bone break did not heal correctly, or in a patient whose growth plate was diseased or damaged prior to maturity. In some patients, stature lengthening is desired, and is achieved by lengthening both femurs and/or both tibia to increase the patient's height.

Bone transport is a similar procedure, in that it makes use of osteogenesis, but instead of increasing the distance between the ends of a bone, bone transport fills in missing bone in between. There are several reasons why significant amounts of bone may be missing. For example, a prior non-union of bone, such as that from a fracture, may have become infected, and the infected section may need to be removed. Segmental defects may be present, the defects often occurring from severe trauma when large portions of bone are severely damaged. Other types of bone infections or osteosarcoma may be other reasons for a large piece of bone that must be removed or is missing.

Intramedullary distraction devices and bone transport devices have been devised which can be adjusted non-invasively, using a variety of mechanisms such as magnets, motors, shape memory metals, and hydraulics. These devices are typically cylindrical and have a coaxially arranged, telescopic arrangement, in order to be low profile and allow for placement within the medullary canal of the bone. In these devices, the lengthening mechanism is typically assembled inside a housing, and then held in place by welds, for example, circumferential or axial welds. Welds may be created by laser, electron beam, or several other technologies. Depending on the design, the weld may need to withstand a large amount of stress, for a large number of cycles, and may also need to provide a hermetic seal when the device is implanted in the body of a subject. Typically, the strength of these devices is significantly below a typical solid or tubular trauma nail that is placed intramedullary in the canal of a broken bone. Because of this, patients with intramedullary distraction or bone transport devices must often use crutches and refrain from full walking for several months, in order to minimize the possibility of breakage of their implants.

In addition to intramedullary distraction and bone transport devices, other types of distraction devices are used in orthopedic applications. Examples include spinal distraction devices for treating scoliosis and other spinal deformities, mandible distraction devices for lengthening the jaw in patient with severe micrognathia and other extramedullary devices (attached to external portions of the bone to be lengthened or contoured). Because these devices are also subjected to high stresses and large numbers of cycles, the welds used to construct their housings are also challenged.

Non-invasively adjustable devices for spinal distraction are implanted in a surgical procedure, and then are non-invasively adjusted (e.g. lengthened) at regular intervals, such as monthly or quarterly. It is typical that an X-ray image is taken before and after the lengthening procedure, in order to visualize and confirm the amount of lengthening that has been achieved. If monthly lengthenings are performed, and if images are taken both before and after the lengthening, then at least 24 x-ray images will be taken of that patient in one year. Some surgeons feel that only one image per lengthening procedure (for example, only after the lengthening) is needed, and others feel it might be done even less often. However, more information about the status of the lengthening of the implant is still desirable.

SUMMARY

In one embodiment, a method of assembling a system for manipulating the skeletal system includes obtaining a monolithic member having opposing ends, one end including a housing having an axially extending cavity. A distraction rod is obtained that has opposing ends, a first end having an inner threaded cavity. A rotatable, radially poled magnet is rotationally coupled to a lead screw having threads. The threads of the lead screw are engaged with the threaded cavity of the distraction rod. The magnet and at least a portion of the first end of the distraction rod are inserted into the axially extending cavity such that the distraction rod and the monolithic member are in coaxial relation to one another. The magnet is axially locked in relation to the monolithic member, wherein the axially locked magnet is capable of rotation. The distraction rod is rotationally locked in relation to the monolithic member.

In another embodiment, a method of assembling a system for manipulating the skeletal system includes obtaining a monolithic member having opposing ends, one end including a housing having an axially extending cavity. A distraction rod is obtained that has opposing ends, a first end having an inner threaded cavity. A maintenance member for magnetically attracting at least one pole of a rotatable, radially poled magnet is secured to the monolithic member. The rotatable, radially poled magnet is rotationally coupled to a lead screw having threads. The threads of the lead screw are engaged with the threaded cavity of the distraction rod. The magnet and at least a portion of the first end of the distraction rod are inserted into the axially extending cavity such that the distraction rod and the monolithic member are in coaxial relation to one another. The magnet is axially locked in relation to the monolithic member, wherein the axially locked magnet is capable of rotation.

In another embodiment, a lengthening device for ultrasonic length measurement includes an elongate metallic member having a having opposing ends, one end including an axially extending cavity, the elongate metallic member having a first landmark which is identifiable by ultrasound when the lengthening device is implanted along the skeletal system the subject. The lengthening device further includes a distraction rod having opposing ends and having a second landmark which creates a distinct ultrasonic signature, different from that of the distraction rod, and which is identifiable by ultrasound when the lengthening device is implanted along the skeletal system the subject, wherein a particular amount of axial movement of the distraction rod in relation to the metallic member causes an equal change in the distance between the first landmark and the second landmark.

In another embodiment, a method for measuring a distraction length of a lengthening device using ultrasound includes implanting the lengthening device within a subject, the lengthening device having an elongate metallic member having opposing ends, one end including an axially extending cavity, the elongate metallic member also having a first landmark which is identifiable by ultrasound when the lengthening device is implanted along the skeletal system the subject, the lengthening device further including a distraction rod having opposing ends and having a second landmark which creates a distinct ultrasonic signature, different from that of the distraction rod, and which is identifiable by ultrasound when the lengthening device is implanted along the skeletal system the subject. An ultrasonic probe is placed adjacent the skin of the subject in the vicinity of the first landmark and the second landmark. An ultrasonic image of at least the first landmark and the second landmark is obtained. The actual length between the first landmark and the second landmark is determined based at least in part on the ultrasonic image.

BRIEF DESCRIPTION OF THE DRAWINGS

FIG. 1 illustrates a spinal distraction device having a monolithic rod and housing.

FIG. 2 illustrates the same spinal distraction device in a side view.

FIG. 3 illustrates a sectional view of the spinal distraction device of FIG. 2 along line 3-3.

FIG. 9A illustrates a distraction rod of the spinal distraction device of FIGS. 1-8 having ultrasound scattering marks.

FIG. 10 illustrates a device and method for measuring the amount of distraction length in a spinal distraction device, using only ultrasound imaging.

FIG. 12 illustrates an intramedullary limb lengthening device having a monolithic rod and housing.

FIG. 13 illustrates the same intramedullary limb lengthening device in a side view.

FIG. 14 illustrates a sectional view of the intramedullary limb lengthening device of FIG. 13 along line 14-14.

FIG. 15A illustrates detailed view 15 of FIG. 14.

FIG. 15B illustrates a sectional view of an alternative embodiment of an intramedullary limb lengthening device.

FIG. 15C illustrates a ring gear insert of the embodiment of FIG. 15B.

FIG. 15D illustrates a coupling assembly of the embodiment of FIG. 15B.

FIG. 16 illustrates an exploded view of the intramedullary limb lengthening device of FIGS. 12 through 15A.

FIG. 17 illustrates detailed view 17 of FIG. 16.

FIG. 23 illustrates an assembly being inserted into the monolithic member of the intramedullary limb lengthening device.

FIG. 24 illustrates the assembly of FIG. 23 being pushed further into the monolithic member with a cannulated tool.

DETAILED DESCRIPTION OF THE ILLUSTRATED EMBODIMENTS

Figure 4:
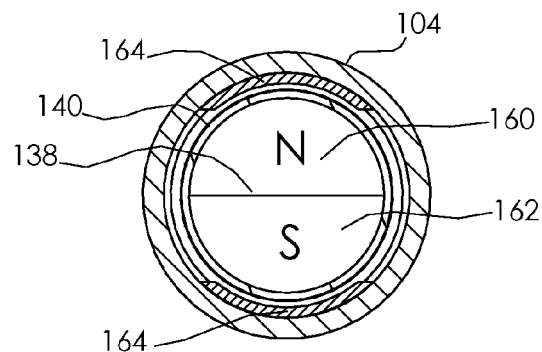
FIG. 4 illustrates a cross-sectional view of the spinal distraction device of FIG. 2 along line 4-4.
Figure 5:
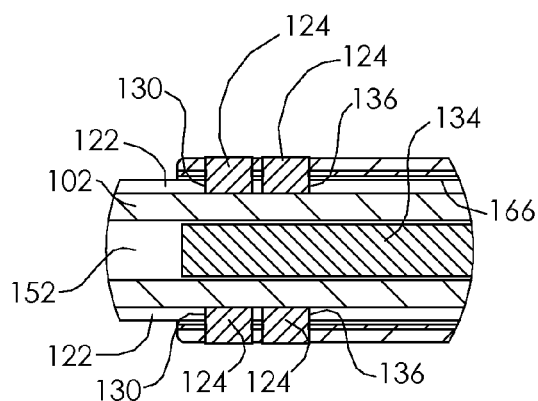
FIG. 5 illustrates detailed view 5 of FIG. 3.

FIGS. 1 and 2 illustrate a spinal distraction device 100 comprising a distraction rod 102 and a monolithic member 104. The monolithic member 104 extends between a first end 110 and a second end 112, and includes a hollow housing 106 and a solid segment 108, as better appreciated in the sectional view of FIG. 3. The monolithic member 104 is formed as a unitary structure with no seams or joints. The distraction rod 102 also includes a solid segment 114 and a hollow segment 116. Like the monolithic member 104, the distraction rod 102 is a unitary structure with no seams or joints connecting various sub-components. Both the distraction rod 102 and the monolithic member 104 may be made from a variety of biocompatible materials, including titanium, Titanium-6Al-4V, cobalt chromium alloys, and stainless steel. Because the distraction rod 102 and the monolithic member 104 are the primary load bearing members of the spinal distraction device 100, and because neither has any external circumferential weld, the spinal distraction device 100 is capable of withstanding improved loading challenges in comparison to standard spinal distraction devices. The solid segment 108 of the monolithic member 104 and the solid segment 114 of the distraction rod 102 have over a majority of their lengths respective diameters or thicknesses that provide a range between about 2.5 mm to about 7.5 mm, and more commonly between about 4.5 mm to about 6.35 mm. These solid segments 108, 114 are configured to allow coupling to pedicle screws and hooks, used for attachment to portions of the vertebrae. They may also have non-circular cross-sections, and in those cases compatible with other types of pedicle screws and hooks.

Figure 6:
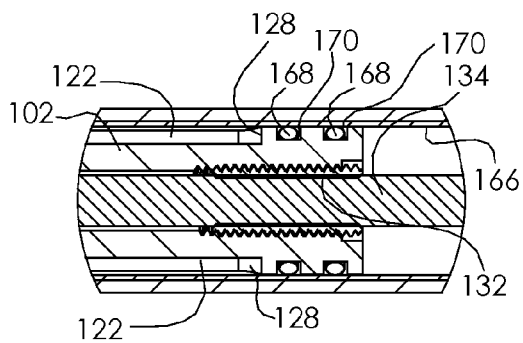
FIG. 6 illustrates detailed view 6 of FIG. 3.
Figure 7:
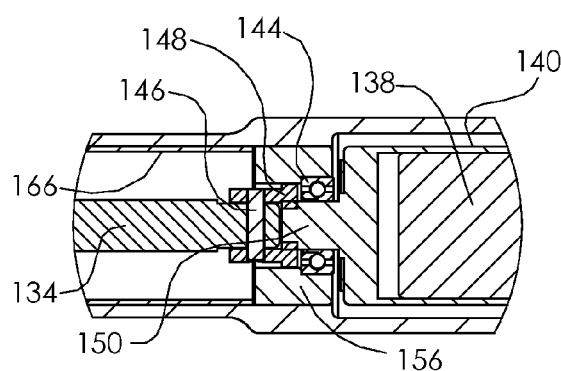
FIG. 7 illustrates detailed view 7 of FIG. 3.
Figure 8:
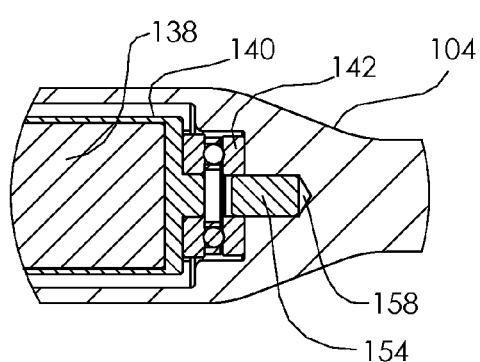
FIG. 8 illustrates detailed view 8 of FIG. 3.

The respective cross-sectional views in FIG. 4 and FIGS. 5 through 8 show more detail of the spinal distraction device 100 in combination with FIGS. 1 through 3. A magnet 138 is a cylindrical, radially-poled rare earth magnet, for example of neodymium-iron-boron. The magnet 138 is enclosed and bonded within a magnet housing 140, which in turn is rotatably contained between a thrust bearing 142 and a radial bearing 144. The magnet 138 may be bonded within the magnet housing 140 by epoxy. The magnet housing 140 is coupled to a lead screw 134 by a pin 146 and a coupler 148. The coupler 148 is welded to an end 150 of the magnet housing 140 and both the coupler 148 and the lead screw 134 have holes through which the pin 146 is placed. The thrust bearing 142 is held over a centering pin 154, which fits into a cavity 158 at an end of the hollow housing 106 of the monolithic member 104. A radial bearing 144 is held within a spacer ring 156. The distraction rod 102 has a first end 118 and a second end 120 and is configured to be telescopically expandable from the hollow housing 106 of the monolithic member 104. A nut 132 is bonded within a cavity 152 of the hollow section 116 of the distraction rod 102, and the lead screw 134 engages the nut 132, so that rotation of the lead screw 134 in a first direction distracts or lengthens the distraction rod 102 and rotation of the lead screw 134 in a second, opposite direction retracts or shortens the distraction rod 102. Two grooves 122 run in an axial direction along the outer wall of the distraction rod 102, from a first end 126 (FIG. 2) to a second end 128 (FIG. 6). Pins 124 are spot welded or attached by other means to the wall of the hollow housing 106 of the monolithic member 104. The pins 124 extend radially into the grooves 122, thus assuring that the distraction rod 102 may not rotate in relation to the monolithic member 104, while also allowing axial extension and retraction of the distraction rod 102 in relation to the monolithic member 104. When the distraction rod 102 is fully retracted, a leading edge 130 of the pin 124 abuts the first end 126 of the groove 122, keeping any further retraction from happening, and avoiding any jamming between the nut 132 and the lead screw 134. When the distraction rod 102 is fully distracted, a leading edge 136 of the pin 124 abuts a second end 128 of the groove 122, thus assuring that the distraction rod 102 remains at least partially within the hollow housing 106 of the monolithic member 104.

Turning to FIG. 4, the magnet 138, comprising a north pole 160 and a south pole 162 is shown as bonded within the magnet housing 140 inside the hollow housing 106 of the monolithic member 104. Two maintenance members 164 are secured to the inner wall of the hollow housing 106 of the monolithic member 104 about 180° from each other along circumference. As shown, maintenance members 164 are curved plates, preferably made from a material such as 400 series stainless steel, which has magnetic properties that allow attraction to the poles 160, 162 of the magnet 138 when closely located. This aligns the magnet 138, as shown, and as the subject moves, the magnet 138 is not allowed to turn, but rather stays in the desired orientation. When distracting the spinal distraction device 100 with a strong external, moving magnetic field, however, the attraction of the magnet 138 to the maintenance members 164 is overcome easily, allowing the magnet 138 to turn. The maintenance members 164 may be resistance welded or adhesive or epoxy bonded to the inner wall of the monolithic member 104. Alternatively, only one maintenance member 164 may be used, allowing attraction to either pole 160 or pole 162 of the magnet 138, but still aligning the magnet 138. In applications where patient movement is not significant, it may not be necessary to include any maintenance members 164.

Figure 20:
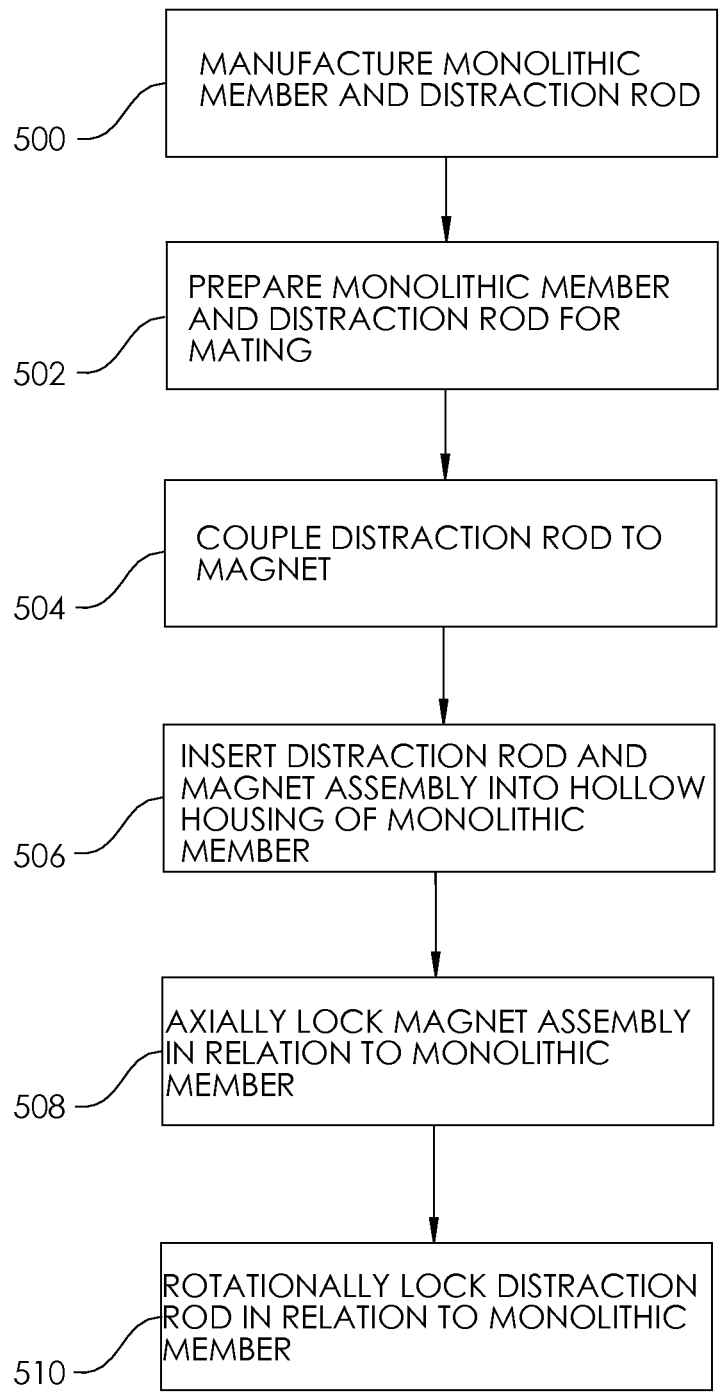
FIG. 20 illustrates a process for assembling a spinal distraction device having improved strength.
Figure 22:
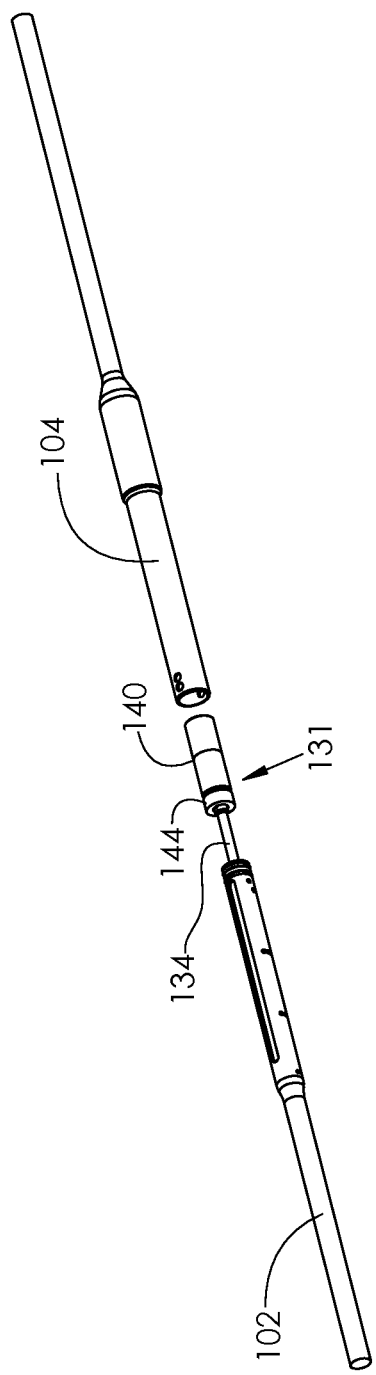
FIG. 22 illustrates a distraction rod and magnetic assembly being inserted into the monolithic member of the spinal distraction device.

The method for assembling the spinal distraction device 100 is illustrated in FIG. 20. In operation 500, the distraction rod 102 and the monolithic member 104 are individually manufactured, for example by machining processes incorporating manual or automated lathes. Included within this manufacturing operation may be the forming of an axially-extending cavity within the monolithic member 104. Post-processing may be included in this operation, for example bead blasting, passivation or anodizing. In operation 502, the distraction rod 102 and the monolithic member 104 are prepared for mating. In this operation, the nut 132 is bonded into the distraction rod 102. One or more o-rings 168 are placed in circumferential cavities 170 of the distraction rod 102. One or more maintenance members 164 are bonded in place. A centering pin 154 is placed into the cavity 158 at the end of the hollow housing 106 of the monolithic member 104. The centering pin 154 may be press fit into the cavity 158, or may be bonded with an adhesive, epoxy or other joining means. The thrust bearing 142 is placed over the centering pin 154. In operation 504, the distraction rod 102 is coupled to the magnet 138. In this operation, the magnet 138 is bonded into the magnet housing 140. The magnet housing 140 may be a two piece assembly, for example a clamshell configuration, or bookends, or a cup/cap configuration. The radial bearing 144 is pressed over the end 150 of the magnet housing 140 and the coupler 148 is welded or bonded to the end 150 of the magnet housing 140. The lead screw 134 is attached to the coupler 148 by the placing the pin 146 through the holes in the coupler 148 and the lead screw 134. The spacer ring 156 is then slid into place over the coupler 148 and the radial bearing 144. The lead screw 134 is screwed into the nut 132. In operation 506, the distraction rod 102 and magnet assembly 131 as seen in FIG. 22 (including magnet 138/magnet housing 140/radial bearing 144/coupler 148/lead screw 134/pin 146/spacer ring 156/nut 132/distraction rod 102) are then inserted into the hollow housing 106 of the monolithic member 104 (see FIG. 22). In operation 508, the magnet assembly 131 is axially locked in place within the hollow housing 106 of the monolithic member 104. More specifically, a sleeve 166 having an outer diameter close to the inner diameter of the hollow housing 106 of the monolithic member 104 is pushed into the hollow housing 106 and either press fit or bonded in place. It may also be resistance welded in place. The sleeve 166 serves to push the assembled items into their desired axial location. When the sleeve 166 is bonded, it then holds the components in this configuration. The two different inner diameter portions of the spacer ring 156 have the appropriate diameters and lengths so that the spacer ring 156 does not contact the magnet housing 140. In operation 510, the distraction rod is rotationally locked in relation to the monolithic member. The sleeve 166 is supplied with holes to match those in the wall of the hollow housing 106 through which the pins 124 are placed. Alternatively, holes may be drilled through the sleeve 166 using the holes in the hollow housing 106 as a guide. The o-rings 168 of the distraction rod 102 serve to seal between the distraction rod 102 and the inner diameter of the sleeve 166. The outer diameter of the sleeve 166 is sealably attached to the inner diameter of the hollow housing 106 via the adhesive or epoxy with which it is attached. Together, these two seals protect the inner contents of the hollow housing 106 of the monolithic member 104 from body fluids.

FIG. 9A is a view of the distraction rod 102 of the spinal distraction device 100 of FIG. 1, having a tapered portion 101, and showing four landmarks 172, 174, 176, 178 for scattering ultrasound. The landmarks may consist of drilled indentations or partial holes, for example drilled with a small end mill. Typical hole diameter is about 1.00 mm, and typical hole depth is about 0.75 mm. In this embodiment, the distraction rod 102 is formed of a metal, for example Titanium 6AL-4V, and thus is very reflective of ultrasound waves, and because of its continuity and smooth surface, a consistent bright line will be seen (see white contour of distraction rod 102 image in FIG. 11). The landmarks 172, 174, 176, 178, for example made with the holes described, serve to break up this continuity, and give a small, but recognizable pattern in an ultrasound image. By using a different number of holes, or a varying array of holes, different image characteristics can be achieved. For example, landmark 172 is a single hole, while landmark 174 is a (in this figure) vertically arrayed pair of holes, with a distance of 1.50 mm from center to center. Landmark 176 consists of three vertically arrayed holes, with a center-to-center distance of adjacent holes of 1.25 mm.

Landmark 178 is two diagonally arrayed holes with a center-to-center distance of 2.75 mm.

FIG. 10 illustrates the spinal distraction device 100 implanted in a subject, and attached to four vertebrae 184 using pedicle screws 182. The spinal distraction device 100 has been lengthened a cumulative total amount of 17.6 mm, and landmarks 172, 174 have been extended from the hollow housing 106 of the monolithic member 104, while landmarks 176, 178 are still inside. The nose 188 of an ultrasound probe 186 is coated with an ultrasound gel and pressed over the skin 190. The ultrasound probe 186 illustrated has a linear array transducer 192 having a span of 40 mm, though probes are also available with spans of up to 64 mm, such as the General Electric L764. Typically, a transducer capable of being run at five to ten MegaHertz (5.0-10.0 MHz) is appropriate for the spinal distraction application, because it will be able to image the spinal distraction device 100 at its typical range of depths, based on patient tissue thickness. As seen in FIG. 10, the ultrasound probe 186 is centered over the region of interest (ROI), and adjusted until an image such as that in FIG. 11 can be visualized. The region of interest in FIG. 10 includes the extended landmarks 172, 174 and the first end 110 of the monolithic member 104. A cable 202 transfers signals back and forth between the linear array transducer 192 and an ultrasound unit 200. Signals are processed in a processor 206, and can be stored in a memory 208. An interface (keyboard, touch screen, etc.) 210 can be manipulated by the user to operate the ultrasound unit 200. The resulting image may be visualized on a display 204. Ultrasound waves 212 are transmitted to the spinal distraction device 100 and reflected waves 214 are received. In a subject 180 with a large amount of fat 194 or one in which the spinal distraction device 100 has been implanted significantly below the muscle 196, it is possible to hold the handle 198 of the ultrasound probe 186 and compress the fat 194, to bring the linear array transducer 192 of the ultrasound probe 186 closer to the spinal distraction device 100, as seen in FIG. 10. This assures that the desired image is located well within the display of the ultrasound unit 200.

Figure 11:
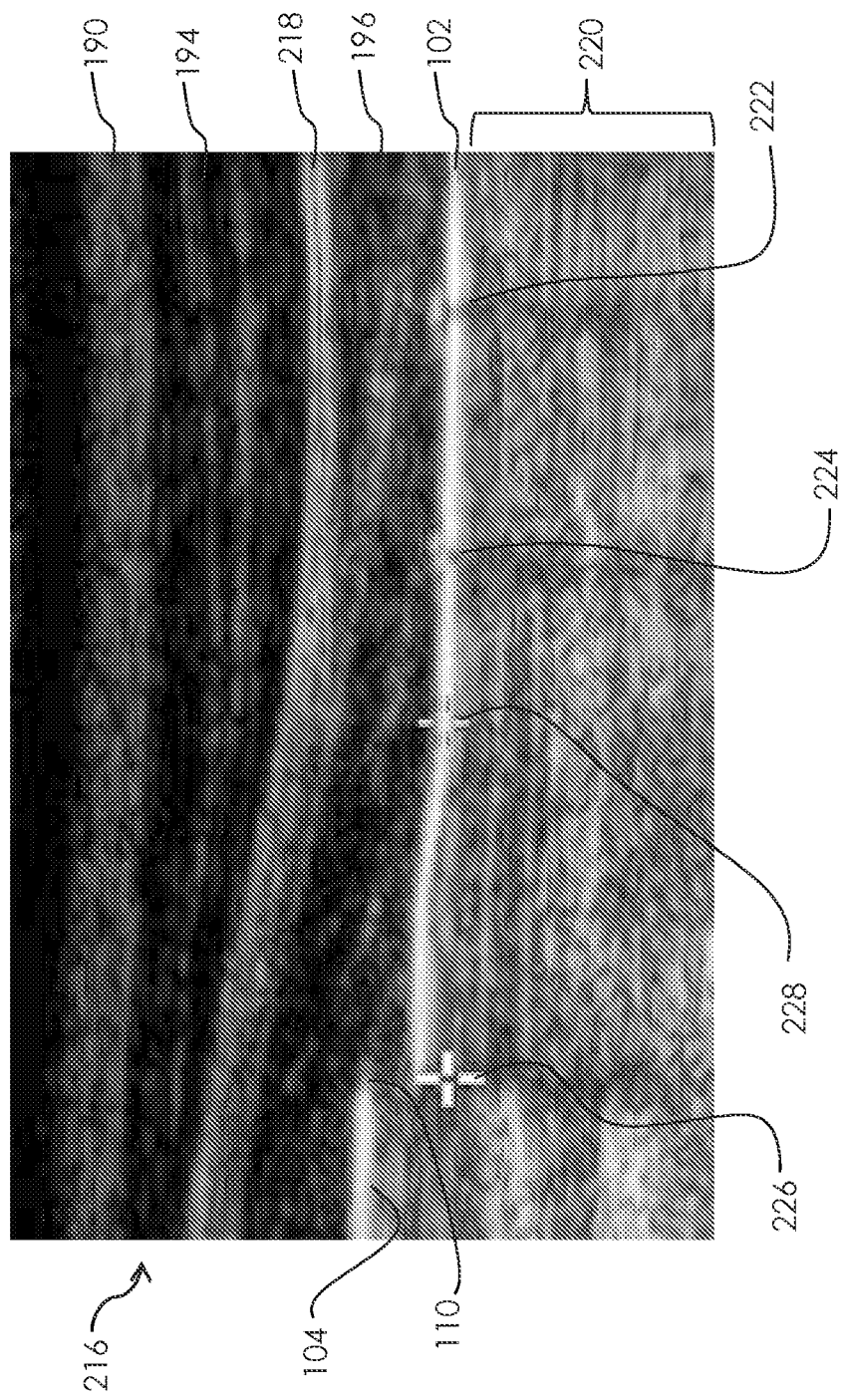
FIG. 11 is an ultrasound image of a spinal distraction device for the purpose of measuring the amount of distraction length.

In FIG. 11, an ultrasound scan 216 was performed using a 40 mm linear array transducer at 8.0 MHz. Skin 190, fat 194, and muscle 196 covered by fascia 218 can be clearly seen, as can the surface of the distraction rod 102, seen in bright white, and the first end 110 of the monolithic member 104. Beneath these features is an area of ultrasonic shadowing 220, due to lack of penetration of the ultrasound wave past the highly reflective titanium of the distraction rod 102 and the monolithic member 104. A first landmark 222 and second landmark 224 are also visible on the ultrasound scan 216. Because the distraction rod 102 and the monolithic member 104 move relative to each other when the spinal distraction device 100 is lengthened or shortened, a measurement should be taken between a landmark on the distraction rod 102 and a landmark on the monolithic member 104. The preferred landmark on the monolithic member 104 is the first end 110, because it is easy to appreciate the drop off in diameter from it to the distraction rod 102 that is seen extending from the monolithic member 104. The user placed a first cursor 226 along the x-axis in line with the first end 110, but on the y-axis at the level of the surface of the distraction rod 102. Varying the y-axis location is not necessary in ultrasound units that give an x distance, y distance and a hypotenuse. A second cursor 228 was then moved to the desired landmark on the distraction rod 102, for example landmark 222 or landmark 224. Many ultrasound units allow for accurate on-screen caliper measurements, but alternatively, the distance between first landmark 222 and second landmark 224, a known, controlled distance, may be used for accurate scaling.

Figure 9B:
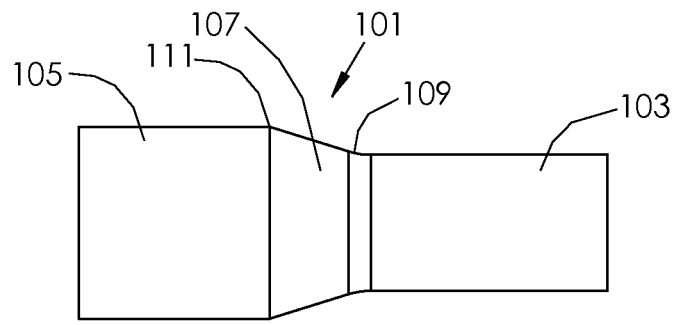
FIG. 9B illustrates a first alternative embodiment for ultrasound scattering.
Figure 9C:
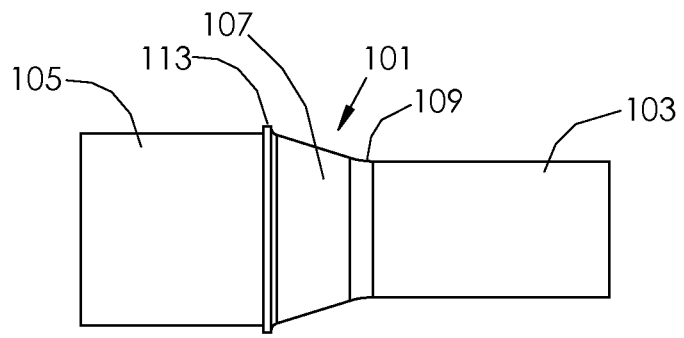
FIG. 9C illustrates a second alternative embodiment for ultrasound scattering.
Figure 9D:
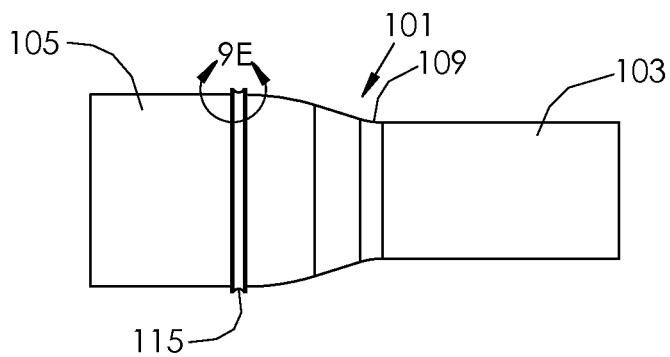
FIG. 9D illustrates a third alternative embodiment for ultrasound scattering.
Figure 9E:
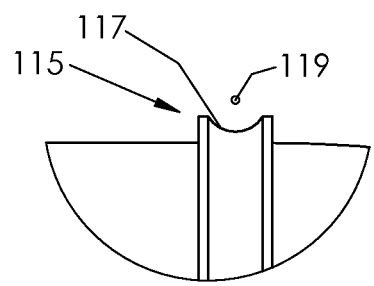
FIG. 9E illustrates detail 9E of the third alternative embodiment for ultrasound scattering of FIG. 9D.

The holes depicted in FIG. 9A may be left open, or they may be filled, for example with epoxy. The epoxy may be doped with ceramic particles, in order to scatter the ultrasound in a still different manner. As an alternative to the landmarks 172, 174, 176, 178 described in FIG. 9A, several alternative embodiments for scattering ultrasound are presented in FIGS. 9B through 9D, particularly depicting tapered portion 101 of distraction rod 102. The tapered portion 101 includes a taper 107 that extends between small diameter segment 103 and large diameter segment 105. Large diameter segment 105 has a typical diameter of about 6.35 mm and small diameter segment 103 has a typical diameter of about 2.5 to 6.0 mm, or more particularly 4.5 mm to 6.0 mm. Between the small diameter segment 103 and that taper 107 is a radiused transition. In FIG. 9B, a sharp transition 111 is formed in the distraction rod 102 at the tapered portion 101. This sharp transition 111 provides a highly defined point in the ultrasound image for making a precision axial measurement. In FIG. 9C, an embodiment is depicted which features a short ridge 113 extending around the distraction rod 102. The ridge 113 also provides a highly defined point for resolving in an ultrasound image. FIG. 9D depicts an embodiment having an ultrasound focusing feature 115 in place of the ridge 113 of FIG. 9C. The ultrasound focusing feature 115, as seen in more detail in FIG. 9E, includes a concave radius 117 extending around the distraction rod 102. Ultrasound reflects at a range of angles along different axial points on the concave radius 117, and the reflected ultrasound from these various reflections meets at a focal point 119, thus creating a recognizable image.

FIGS. 12 and 13 illustrate an intramedullary limb lengthening device 300 comprising a distraction rod 302 and a monolithic member 304. The monolithic member 304 extends between a first end 310 and a second end 312, as better appreciated in the sectional view of FIG. 14. The monolithic member 304 is formed as a unitary structure with no seams or joints. The distraction rod 302 has a first end 318 and a second end 320, and is configured to be telescopically extendable and retractable within the monolithic member 304. Like the monolithic member 304, the distraction rod 302 is a unitary structure with no seams or joints connecting various sub-components. Both the distraction rod 302 and the monolithic member 304 may be made from a variety of biocompatible materials, including titanium, for example Titanium-6AL-4V, cobalt chromium alloys, and stainless steel. Because the distraction rod 302 and the monolithic member 304 are the primary load bearing members of the intramedullary limb lengthening device 300, and because neither has any external circumferential weld, the intramedullary limb lengthening device 300 is capable of withstanding improved loading challenges in comparison to standard intramedullary limb lengthening devices. The monolithic member 304 contains two transverse holes 301 for passing bone screws, with which to attach the intramedullary limb lengthening device 300 to the bone. The distraction rod 302 contains three transverse holes 303, also for the passing of bone screws. At the second end 312 of the monolithic member 304, a coupling feature 323, provides an interface to releasably engage with an insertion instrument, such as a drill guide. The drill guide may include a male thread and the coupling feature 323 may be provided with a complementary female thread. The intramedullary limb lengthening device 300 comprises a magnet 338 which is bonded within a magnet housing 340 and configured for rotation between a radial bearing 344 and a thrust bearing 342. Between the thrust bearing 342 and the magnet housing 340 are three planetary gear stages 305, 307, 309, as seen in FIG. 15A. The planetary gear stages 305, 307, 309 each comprise a sun gear 311A, 311B, 311C and three planetary gears 313, which are rotatably held within a frame 315 by pins 317. The sun gear 311 is either a part of the magnet housing 340, as in the case of the sun gear 311A of planetary gear stage 305, or a part of the frame 315, as in sun gear 311B or stage 307 and sun gear 311C of gear stage 309. The rotation of the sun gear 311 causes the planetary gears 313 to rotate and track along inner teeth 321 of a ring gear insert 319. Each gear stage 305, 307, 309 has a gear reduction of 4:1, with a total gear reduction of 64:1.

The frame 315 of the final gear stage 309 passes through the thrust bearing 342 and is attached to a lead screw coupler 366 such that rotation of the frame 315 of the final gear stage 309 causes one-to-one rotation of the lead screw coupler 366. The lead screw coupler 366 and a lead screw 358 each contain transverse holes through which a locking pin 368 is placed, thus rotationally coupling the lead screw 358 to the final gear stage 309. A locking pin retainer 350 is slid over and tack welded to the lead screw coupler 366 to radially maintain the locking pin 368 in place. The distraction rod 302 has an internally threaded end 363, into which external threads 365 of a nut 360 are threaded and bonded, for example with epoxy. The nut 360 has internal threads 367 which are configured to threadably engage with external threads 325 of the lead screw 358, thereby allowing rotation of the lead screw 358 to distract the distraction rod 302 in relation to the monolithic member 304. Rotation of the magnet 338 and the magnet housing 340 causes rotation of the lead screw at ¹⁄₆₄ the rotational speed, but with significantly increased torque (64 times, minus frictional losses), and thus an amplified distraction force. O-rings 362 are placed in ring grooves 388 on exterior of the distraction rod 302 and create a dynamic seal between the monolithic member 304 and the distraction rod 302, thus protecting the internal contents from body fluids. A split washer stop 364, located between the distraction rod 302 and the lead screw coupler 366, guards against jamming that would otherwise be caused as the distraction rod 302 approaches the lead screw coupler 366, for example if intramedullary limb lengthening device 300 is fully retracted with a high torque applied by an external moving magnetic field.

A maintenance member 346, comprising a curved plate made from 400 series stainless steel, is bonded within the inner wall of the monolithic member 304 by epoxy, adhesive, resistance welding or other suitable process. The maintenance member 346 attracts a pole of the magnet 338, thus keeping the limb lengthening device 300 from being accidentally adjusted by movements of the patient. However, a strong moving magnetic field, such as that applied by magnetic adjustment devices known in the art, is capable of overcoming the attraction of the magnet 338 to the maintenance member 346 in order to rotate the magnet 338 and adjust the length of the intramedullary limb lengthening device 300. Maintenance member has a thickness of approximately 0.015 inches and spans a circumferential arc of less than 180°. An exemplary arc is 99°.

Figure 21:
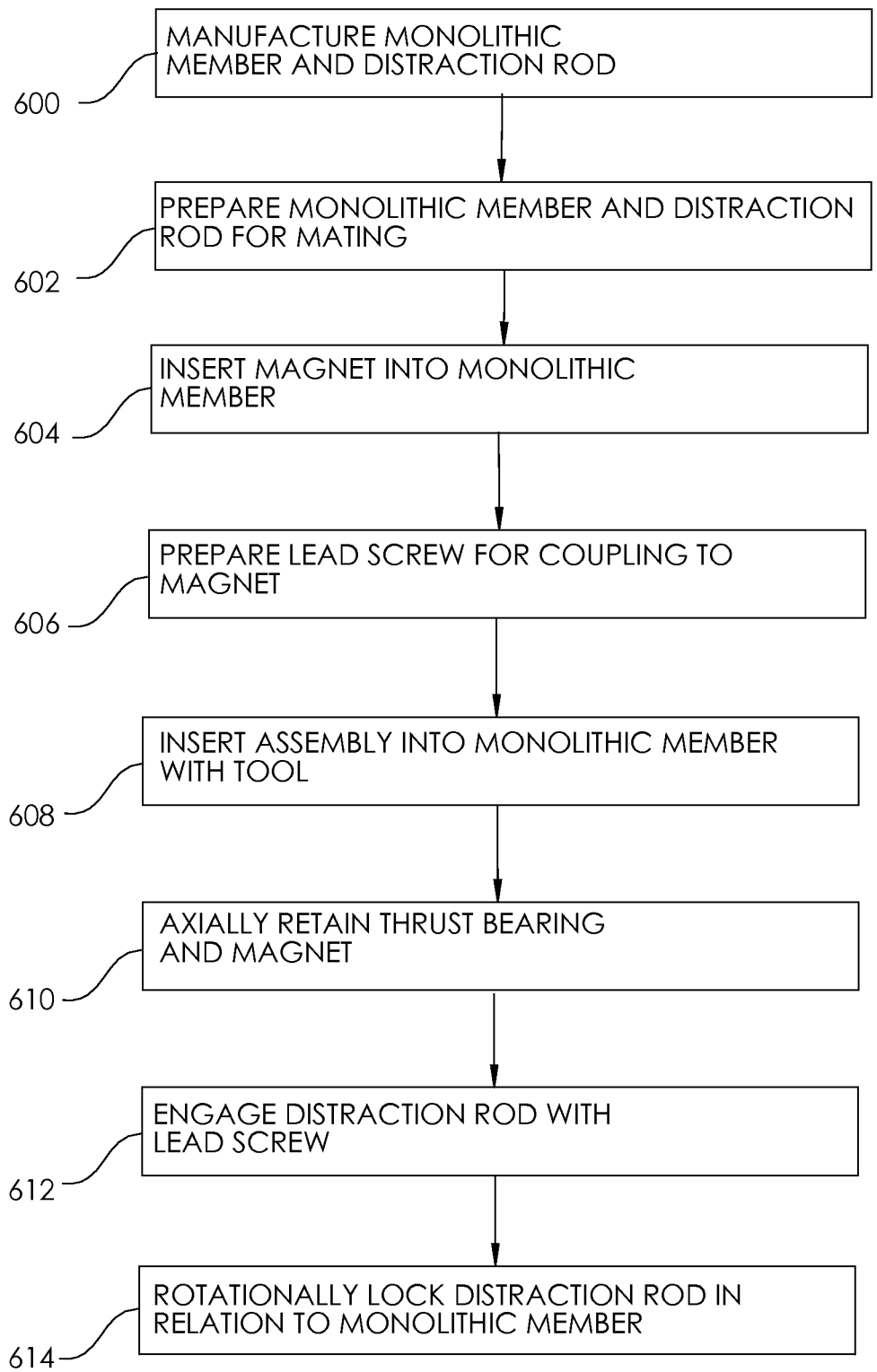
FIG. 21 illustrates a process for assembling an intramedullary limb lengthening device having improved strength.

The method for assembling the intramedullary limb lengthening device 300 is illustrated in FIG. 21. These assembly operations and the design of the internal components make it possible to incorporate the monolithic member 304 into the design of the intramedullary limb lengthening device 300. In operation 600, the distraction rod 302 and the monolithic member 304 are individually manufactured, for example by machining processes incorporating manual or automated lathes. Included within this manufacturing operation may be the forming of an axially-extending cavity within the monolithic member 304. Post-processing may be included in this operation, for example bead blasting, passivation or anodizing. In operation 602, the distraction rod 302 and the monolithic member 304 are prepared for mating. In this operation, the nut 360 is bonded into the distraction rod 302 and the o-rings 362 are placed into the ring grooves 388 as described. The maintenance member 346 is bonded to the monolithic member 304. In operation 604, the magnet 338 is placed into the cavity 390 of the monolithic member 304. In this operation the magnet 338 and the magnet housing 340 are bonded together, and then assembled with the radial bearing 344 into the monolithic member 304 (see FIG. 14). Prior to assembling the radial bearing 344 into the monolithic member, the longitudinal depth of the cavity 390 of the monolithic member 304 is measured, and, if necessary, one or more shims may be placed before the radial bearing 344 so that the resultant axial play in the assembled components is not so low as to cause binding, yet not so high as to risk disassembly. In operation 606, the lead screw 358 is prepared for coupling to the magnet 338 that is in the cavity 390 of the monolithic member 304. In this operation the ring gear insert 319 is slid into the cavity 390 of the monolithic member 304 until it abuts a ledge 392. First and second planetary gear stages 305, 307 are then placed into assembly as seen in FIG. 15A. The locking pin retainer 350 is preloaded over the lead screw coupler 366 prior to welding the lead screw coupler 366 to the final planetary gear stage 309, and is then slid in place over the locking pin 368 after the locking pin 368 is placed. Final planetary gear stage 309 is inserted through the thrust bearing 342 and is welded to the lead screw coupler 366, allowing for some axial play of the thrust bearing 342. The split washer stop 364 is then placed onto the lead screw 358. The lead screw 358 is then attached to the lead screw coupler 366 with the locking pin 368, and then the locking pin retainer 350 is slid over a portion of the ends of the locking pin 368 and tack welded to the lead screw coupler 366. Thrust bearing retainers 354, 356 are two matching pieces which form a cylindrical clamshell around the thrust bearing 342 and the lead screw coupler 366. The internal diameter of the monolithic member 304 is tinned with solder, as are the outer half diameter surfaces of each of the thrust bearing retainers 354, 356. In operation 608, the thrust bearing retainers 354, 356 are then clamped over an assembly 327 (illustrated in FIG. 23) containing the thrust bearing 342, lead screw coupler 366, planetary gear stage 309, and lead screw 358, and the thrust bearing retainers 354, 356 and the assembly 327 are pushed together into place within the monolithic member with a cannulated tool 329 (see FIGS. 23 and 24). The cannulated tool 329 has a chamfered end 331 which pushes against a matching chamfer 352 in each of the thrust bearing retainers 354, 356, thus forcing them outward against the inner diameter of the monolithic member 304. The sun gear 311C of the final planetary gear stage 309 engages with the planet gears 313 of the final planetary gear stage 309 and then chamfered edges 394 of the thrust bearing retainers 354, 356 are pushed against a chamfer 348 of the ring gear insert 319 with a pre-load force. In operation 610, the thrust bearing 342 and the magnet 338 are axially retained. In this operation, the thrust bearing retainers 354, 356 are soldered to the monolithic member 304 at the tinned portions, thus maintaining the pre-load force in place. This may be accomplished using induction heating. The friction of the ledge 392 and the chamfered edge 394 against opposing ends of the ring gear insert 319, as well as the wedging between the chamfered edge 394 and the chamfer 348, hold the ring gear insert 319 rotationally static in relation to the monolithic member 304. Alternatively, the ring gear insert 319 may have a keyed feature that fits into a corresponding keyed feature in the monolithic member 304, in order to stop the ring gear insert 319 from being able to turn in relation to the monolithic member 304, in case the friction on the ends of the ring gear insert 319 is not sufficient to hold it static.

In operation 612, the distraction rod 302 is engaged with the lead screw 358. In this operation an assembly tool consisting of a high speed rotating magnet is used to make the magnet 338 and thus the lead screw 358 rotate and the distraction rod 302 is inserted into the monolithic member 304 while the lead screw 358 engages and displaces in relation to the nut 360 of the distraction rod 302. After the distraction rod 302 is inserted into the monolithic member 304 as described and retracted at least somewhat, the distraction rod 302 is still free to rotate in relation to the monolithic member 304. For the stability of the bone pieces being distracted it is desired to inhibit rotation between the distraction rod 302 and the monolithic member 304, and this final portion of the assembly process is described in relation to FIGS. 16 and 17. In operation 614, the distraction rod 302 is rotationally locked in relation to the monolithic member 304. In this operation, an anti-rotation ring 370 is placed over the distraction rod 302 by engaging protrusions 374, one on each side, into grooves 372 extending along the distraction rod 302 and then by sliding the anti-rotation ring 370 up to a tapered inner edge 376 of the monolithic member 304. The anti-rotation ring 370 and the distraction rod 302 are then rotated until guide fins 382 can be inserted into guide cuts 380 in end of the monolithic member 304. The anti-rotation ring 370 is now axially snapped into the monolithic member 304 as a flat edge 384 of the anti-rotation ring 370 is trapped by an undercut 378. The undercut 378 has a minimum diameter which is less than the outer diameter of the flat edge 384 of the anti-rotation ring 370, and is temporarily forced open during the snapping process. As assembled, the anti-rotation ring 370, the monolithic member 304 and the distraction rod 302 are all held rotationally static in relation to each other. In addition, when the intramedullary limb lengthening device 300 reaches maximum distraction length, the ends 386 of grooves 372 abut the protrusions 374, and thus the distraction rod 302 is kept from falling out of the monolithic member 304.

An alternative embodiment of the intramedullary limb lengthening device 300 of FIGS. 12-15A is shown in a sectional view in FIG. 15B. Much of this embodiment is identical to the embodiment of FIGS. 12-15A, however the differences are hereby described. The embodiment does not have thrust bearing retainers 354, 356, but instead incorporates a thrust bearing ferrule 335 having an external tapered end 347. A thrust bearing retainer 337, a locking pin retainer 341 and the thrust bearing ferrule 335 are placed over the thrust bearing 342 and a lead screw coupler 339, and the final planetary gear stage 309 is inserted through the thrust bearing 342 and is welded to the lead screw coupler 339. As shown in FIG. 15D, the locking pin retainer 341 has a relief 361 to allow the passage of the locking pin 368. After the locking pin 368 is placed, the locking pin retainer 341 is rotated so that the relief 361 is no longer directly over the locking pin 368 and the locking pin retainer 341 is tack welded or secured by other methods to the lead screw coupler 339, thus retaining the locking pin 368. These assembled components are then inserted into the cavity 390 of the monolithic member 304, where the final planetary gear stage 309 is coupled to the other planetary gear stages 305, 307 and the magnet 338. In this embodiment, a ring gear insert 333 (FIG. 15C) has an indentation 351 on each side. A tab 349 on each side of the thrust bearing ferrule 335 inserts into each indentation 351, in order to inhibit rotation of the ring gear insert 333 in relation to the monolithic member 304, once the thrust bearing ferrule 335 is engaged into the monolithic member 304. Also in this embodiment, the monolithic member 304 contains internal threading 343. The engagement of the thrust bearing ferrule 335 is achieved by tightening external threading 345 of the thrust bearing retainer 337 into the internal threading 343 of the monolithic member 304. A tool (not shown) is engaged into cut outs 357 on each side of the thrust bearing retainer 337 and is used to screw the thrust bearing retainer 337 into the internal threading 343 of the monolithic member 304. As shown in FIG. 15B, this wedges an internal taper 353 of the thrust bearing retainer 337 against the external tapered end 347 of the thrust bearing ferrule 335, allowing the thrust bearing ferrule 335 to apply a controlled load on the ring gear insert 333, locking the ring gear insert 333 axially and rotationally in relation to the monolithic member 304. The thrust bearing retainer 337 contains an axial split on the opposite side (not shown). The split in the thrust bearing retainer 337, allows the outer diameter of the thrust bearing retainer 337 to be slightly reduced (by compression) while it is inserted into the monolithic member 304, prior to being threaded, so that the internal portion of the monolithic member 304 is not scratched during insertion. A ledge 355 is visible on the lead screw coupler 339 in FIG. 15D. As noted earlier, the split washer stop 364 butts up against this ledge 355 to prohibit jamming when the distraction rod 302 is retracted completely.

Figure 18:
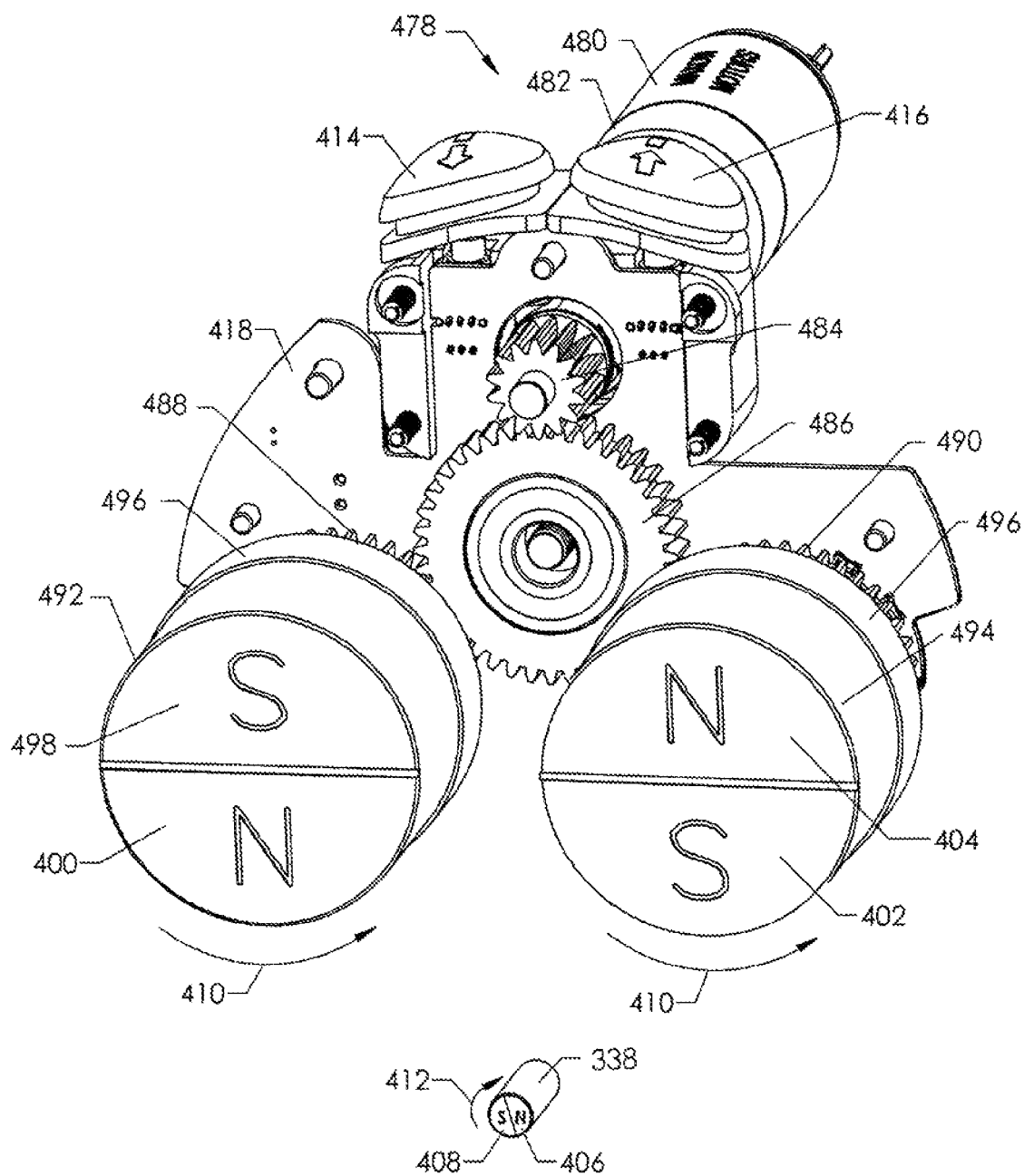
FIG. 18 illustrates internal components of an external adjustment device for non-invasively adjusting an intramedullary limb lengthening device according to one embodiment.
Figure 19:
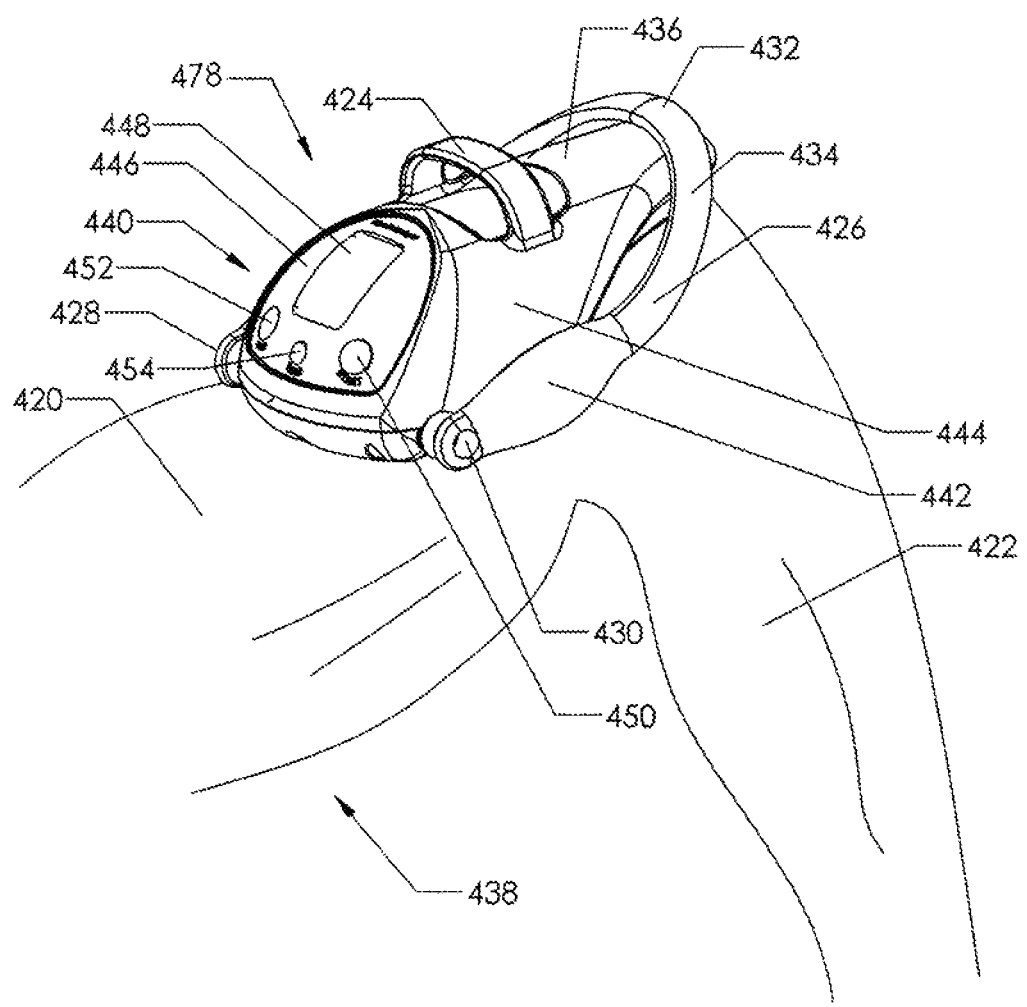
FIG. 19 illustrates an external adjustment device in a configuration for adjusting an intramedullary limb lengthening device implanted within the femur.

FIGS. 18 and 19 illustrate an external adjustment device 478 configured for applying a moving magnetic field to allow for non-invasive adjustment of the intramedullary limb lengthening device 300 by turning the magnet 338 within the intramedullary limb lengthening device 300. FIG. 18 illustrates the internal components of the external adjustment device 478, and for clear reference, shows the magnet 338 of the intramedullary limb lengthening device 300, without the rest of the assembly. The internal working components of the external adjustment device 478 may, in certain embodiments, be similar to that described in U.S. Patent Application Publication No. 2012/0004494, which is incorporated by reference herein. A motor 480 with a gear box 482 outputs to a motor gear 484. The motor gear 484 engages and turns a central (idler) gear 486, which has the appropriate number of teeth to turn first and second magnet gears 488, 490 at identical rotational speeds. First and second magnets 492, 494 turn in unison with the first and second magnet gears 488, 490, respectively. Each magnet 492, 494 is held within a respective magnet cup 496 (shown partially). An exemplary rotational speed is 60 RPM or less. This speed range may be desired in order to limit the amount of current density induced in the body tissue and fluids, to meet international guidelines or standards. As seen in FIG. 18, the south pole 498 of the first magnet 492 is oriented the same as the north pole 404 of the second magnet 494, and likewise, the first magnet 492 has its north pole 400 oriented the same as the south pole 402 of the second magnet 494. As these two magnets 492, 494 turn synchronously together, they apply a complementary and additive moving magnetic field to the radially-poled, magnet 338, having a north pole 406 and a south pole 408. Magnets having multiple north poles (for example, two) and multiple south poles (for example, two) are also contemplated in each of the devices. As the two magnets 492, 494 turn in a first rotational direction 410 (e.g., counter-clockwise), the magnetic coupling causes the magnet 338 to turn in a second, opposite rotational direction 412 (e.g., clockwise). The rotational direction of the motor 480 is controlled by buttons 414, 416. One or more circuit boards 418 contain control circuitry for both sensing rotation of the magnets 492, 494 and controlling the rotation of the magnets 492, 494.

FIG. 19 shows the external adjustment device 478 for use with an intramedullary limb lengthening device 300 placed in the femur. The external adjustment device 478 has a first handle 424 attached to a housing 444 for carrying or for steadying the external adjustment device 478, for example, steadying it against an upper leg 420, as in FIG. 19, or against a lower leg 422 in the case that the intramedullary limb lengthening device 300 is implanted in the tibia. An adjustable handle 426 is rotationally attached to the external adjustment device 478 at pivot points 428, 430. The pivot points 428, 430 have easily lockable/unlockable mechanisms, such as a spring loaded brake, ratchet or tightening screw, so that a desired angulation of the adjustable handle 426 in relation to the housing 444 can be adjusted and locked in orientation. The adjustable handle 426 is capable of being placed in multiple positions. In FIG. 19, adjustable handle 426 is set so that the apex 432 of loop 434 rests against housing end 436. In this position, patient 438 is able to hold onto one or both of grips 440, 442 while the adjustment is taking place. Patient is able to clearly view a control panel 446 including a display 448. In a different configuration from the two directional buttons 414, 416 in FIG. 18, the control panel 446 includes a start button 450, a stop button 452 and a mode button 454. Control circuitry contained on circuit boards 418 may be used by the surgeon to store important information related to the specific aspects of each particular patient. For example, in some patients an implant may be placed antegrade into the tibia. In other patients the implant may be placed either antegrade or retrograde into the femur. By having the ability to store information of this sort that is specific to each particular patient within the external adjustment device 478, the external adjustment device 478 can be configured to direct the magnets 492, 494 to turn in the correct direction automatically, while the patient need only place the external adjustment device 478 at the desired position, and push the start button 450. The information of the maximum allowable distraction length per day and per distraction session can also be input and stored by the surgeon for safety purposes. These may also be added via an SD card or USB device, or by wireless input. An additional feature is a camera at the portion of the external adjustment device 478 that is placed over the skin. For example, the camera may be located between the first magnet 492 and the second magnet 494. The skin directly over the implanted magnet 338 may be marked with indelible ink. A live image from the camera is then displayed on the display 448 of the control panel 446, allowing the user to place the first and second magnets 492, 494 directly over the area marked on the skin. Crosshairs can be overlayed on the display 448 over the live image, allowing the user to align the mark on the skin between the crosshairs, and thus optimally place the external adjustment device 478.

As described in conjunction with the spinal distraction device 100 of FIGS. 1 through 8 and with the intramedullary limb lengthening device 300 of FIGS. 12-17, load-bearing orthopedic devices can be constructed which, by incorporating a monolithic member 104, 304 having a unitary structure with no seams or joints, have improved strength over prior art devices having welded joints. Four point bend testing of monolithic members 304 constructed in accordance with the methods described herein showed that a strength improvement of 38% was achieved as compared to data obtained on elongate members which incorporated a housing having a laser weld. Additionally, the embodiments for the spinal distraction device 100 and the intramedullary limb lengthening device 300 described herein have features which inhibit rotation between the distraction rod 102, 302 and the monolithic member 104, 304, maintain the magnet 138, 338 in its axial position in relation to the monolithic member 104, 304, and keep the distraction rod 102, 302 from falling out of the monolithic member 104, 304 by providing a stopping mechanism at full extension. All of these features were not achievable in prior devices without resorting to welds which decreased the overall strength.

While embodiments of the present invention have been shown and described, various modifications may be made without departing from the scope of the present invention. For example, the magnets in the devices may be replaced by any type of drive member, for example motors or shape memory mechanisms. They may also be replaced by a subcutaneous lever that allows the device to be non-invasively adjusted. The invention, therefore, should not be limited, except to the following claims, and their equivalents.

What is claimed is:

1. A method of assembling a system for manipulating portions of the skeletal system of a subject, the method comprising:
    obtaining a monolithic member having a first end and a second end, the first end configured for attachment to a first portion of the skeletal system and the second end comprising a housing having an axially extending cavity;
    obtaining a distraction rod having a first end and a second end, the first end having an inner threaded cavity extending along at least a portion of a length thereof, the first end configured to be coaxial and movable within the axially extending cavity and the second end configured to extend from the axially extending cavity and configured for attachment to a second portion of the skeletal system;
    rotationally coupling a rotatable, radially poled magnet to a lead screw having threads such that rotation of the magnet causes rotation of the lead screw;
    engaging the threads of the lead screw with the threaded cavity of the distraction rod;
    inserting the magnet and at least a portion of the first end of the distraction rod into the axially extending cavity such that the distraction rod and the monolithic member are in coaxial relation to one another;
    axially locking the magnet in relation to the monolithic member, wherein the axially locked magnet is capable of rotation; and
    rotationally locking the distraction rod in relation to the monolithic member.

2. The method of claim 1, wherein the rotationally locking operation further includes limiting axial movement of the distraction rod in relation to the monolithic member.

3. The method of claim 1, wherein one full rotation of the magnet causes one full rotation of the lead screw.

4. The method of claim 1, further comprising the operation of forming a dynamic seal located between the distraction rod and the monolithic member, the dynamic seal configured to inhibit body fluids from entering the axially extending cavity.

5. The method of claim 1, further comprising the operation of placing an anti-rotation member in proximity with the monolithic member, the anti-rotation member configured to limit relative rotation between the monolithic member and the distraction rod, while allowing relative axial movement between the monolithic member and the distraction rod.

6. The method of claim 5, wherein the anti-rotation member is further configured to stop the relative axial movement between the monolithic member and the distraction rod at or near a maximum extension of the distraction rod.

7. The method of claim 6, wherein the distraction rod comprises at least one axially extending groove and wherein the anti-rotation member comprises at least one protrusion configured to extend into the groove.

8. The method of claim 1, further comprising the operation of forming one or more landmarks on at least a portion of the distraction rod, the one or more landmarks configured for scattering ultrasound.

9. The method of claim 8, wherein the one or more landmarks comprise one or more holes located at a surface of the distraction rod.

10. The method of claim 8, wherein the one or more landmarks comprise a raised ridge extending around the distraction rod.

11. A method of assembling a system for manipulating portions of the skeletal system of a subject, the method comprising:
   obtaining a monolithic member having a first end and a second end, the first end configured for attachment to a first portion of the skeletal system and the second end comprising a housing having an axially extending cavity;
   obtaining a distraction rod having a first end and a second end, the first end having an inner threaded cavity extending along at least a portion of a length thereof, the first end configured to be coaxial and movable within the axially extending cavity and the second end configured to extend from the axially extending cavity and configured for attachment to a second portion of the skeletal system;
   securing a maintenance member to the monolithic member, the maintenance member configured to magnetically attract at least one pole of a rotatable, radially poled magnet;
   rotationally coupling the rotatable, radially poled magnet to a lead screw having male threads such that rotation of the magnet causes rotation of the lead screw;
   engaging the threads of the lead screw with the threaded cavity of the distraction rod;
   inserting the magnet and at least a portion of the first end of the distraction rod into the axially extending cavity such that the distraction rod and the monolithic member are in coaxial relation to one another; and
   axially locking the magnet in relation to the monolithic member, wherein the axially locked magnet is capable of rotation.

12. The method of claim 11, further comprising the operation of rotationally locking the distraction rod in relation to the monolithic member.

13. The method of claim 12, wherein the rotationally locking operation further includes limiting axial movement of the distraction rod in relation to the monolithic member.

14. The method of claim 11, wherein one full rotation of the magnet causes one full rotation of the lead screw.

15. The method of claim 11, further comprising the operation of forming a dynamic seal located between the distraction rod and the monolithic member, the dynamic seal configured to inhibit body fluids from entering the axially extending cavity.

16. The method of claim 11, further comprising the operation of placing an anti-rotation member in proximity with the monolithic member, the anti-rotation member configured to limit relative rotation between the monolithic member and the distraction rod, while allowing relative axial movement between the monolithic member and the distraction rod.

17. The method of claim 16, wherein the anti-rotation member is further configured to stop the relative axial movement between the monolithic member and the distraction rod at or near a maximum extension of the distraction rod.

18. The method of claim 17, wherein the distraction rod comprises at least one axially extending groove and wherein the anti-rotation member comprises at least one protrusion configured to extend into the groove.

19. The method of claim 11, wherein the maintenance member comprises 400 series stainless steel.

20. The method of claim 11, wherein the axially locking step utilizes induction heating.

* * * * *